US010420454B2

(12) United States Patent
Lichtenstein

(10) Patent No.: US 10,420,454 B2
(45) Date of Patent: Sep. 24, 2019

(54) HOLLOW PROBE WITH SLEEVE

(71) Applicant: OTTek Ltd., Nazareth (IL)

(72) Inventor: Yoav Lichtenstein, Had Hasharon (IL)

(73) Assignee: OTTEK LTD., Nazareth (IL)

( * ) Notice: Subject to any disclaimer, the term of this patent is extended or adjusted under 35 U.S.C. 154(b) by 0 days.

(21) Appl. No.: 15/304,574

(22) PCT Filed: Nov. 9, 2015

(86) PCT No.: PCT/IL2015/051077
§ 371 (c)(1),
(2) Date: Oct. 17, 2016

(87) PCT Pub. No.: WO2016/075682
PCT Pub. Date: May 19, 2016

(65) Prior Publication Data
US 2017/0265724 A1    Sep. 21, 2017

Related U.S. Application Data

(60) Provisional application No. 62/077,923, filed on Nov. 11, 2014.

(51) Int. Cl.
*A61B 1/04* (2006.01)
*A61B 1/00* (2006.01)
(Continued)

(52) U.S. Cl.
CPC ...... *A61B 1/00135* (2013.01); *A61B 1/00068* (2013.01); *A61B 1/00082* (2013.01);
(Continued)

(58) Field of Classification Search
CPC ............ A61B 1/00151; A61B 1/00156; A61B 1/0016; A61B 1/00135
(Continued)

(56) References Cited

U.S. PATENT DOCUMENTS 4,321,915 A  *  3/1982  Leighton ............ A61B 1/00151
                                                 600/114
4,615,331 A     10/1986 Kramann
(Continued)

OTHER PUBLICATIONS

International Search Report dated Feb. 10, 2016 for International Application No. PCT/IL2015/051077 filed Nov. 9, 2015, pp. 1-3.
(Continued)

*Primary Examiner* — Matthew J Kasztejna
(74) *Attorney, Agent, or Firm* — Paul D. Bianco; Fleit Gibbons Gutman Bongini & Bianco PL

(57) ABSTRACT

An endoscopic probe which advances within a lumen having a central valve unit. The valve unit has a central bore defining a proximal end and a distal end, and at least one valve for controlling the introduction and withdrawal of fluid into the central bore. The probe further includes a sliding tubular sheath movably disposed inside the central valve unit, and a flexible sleeve, impermeable to the fluid and sealingly anchored to the central valve unit on both distal proximal ends. The sleeve is folded over to cover both the inside and outside of the sheath to sealingly envelop the sheath and contain the fluid, together with said valve unit, while allowing sliding of the sheath. A method for providing, assembling and operating the probe is also provided.

36 Claims, 23 Drawing Sheets

(51) Int. Cl.
  *A61B 1/31* (2006.01)
  *A61B 1/12* (2006.01)
  *A61B 1/005* (2006.01)
(52) U.S. Cl.
  CPC ............ *A61B 1/00151* (2013.01); *A61B 1/04* (2013.01); *A61B 1/12* (2013.01); *A61B 1/31* (2013.01); *A61B 1/0057* (2013.01)
(58) Field of Classification Search
  USPC .................. 600/114, 121; 604/65.01, 271
  See application file for complete search history.

(56) References Cited

U.S. PATENT DOCUMENTS

| | | | | |
|---|---|---|---|---|
| 4,871,358 A * | 10/1989 | Gold | .................. | A61M 25/0119 604/271 |
| 5,045,070 A * | 9/1991 | Grodecki | ........... | A61B 1/00142 604/271 |
| 5,163,927 A * | 11/1992 | Woker | ................ | A61B 1/00151 604/271 |
| 5,236,423 A * | 8/1993 | Mix | .................... | A61B 1/00151 600/115 |
| 5,259,364 A * | 11/1993 | Bob | .......................... | A61B 1/31 600/115 |
| 5,364,345 A * | 11/1994 | Lowery | .............. | A61M 25/0119 600/116 |
| 5,454,364 A * | 10/1995 | Kruger | ............... | A61B 1/00082 600/114 |
| 5,586,968 A * | 12/1996 | Grundl | ................ | A61B 1/00151 600/114 |
| 6,077,219 A * | 6/2000 | Viebach | .............. | A61B 1/00151 600/114 |
| 6,485,409 B1 * | 11/2002 | Voloshin | ............ | A61B 1/00147 600/101 |
| 6,554,793 B1 | 4/2003 | Pauker et al. | | |
| 6,702,735 B2 | 3/2004 | Kelly | | |
| 2003/0114803 A1 | 6/2003 | Lerner | | |
| 2003/0208223 A1 * | 11/2003 | Kleiner | ............... | A61B 1/00151 606/198 |
| 2004/0143161 A1 | 7/2004 | Baror et al. | | |
| 2004/0243144 A1 | 12/2004 | Bonadio et al. | | |
| 2006/0252989 A1 | 11/2006 | Bar-Or et al. | | |
| 2008/0221390 A1 | 9/2008 | Bob | | |
| 2010/0204546 A1 | 8/2010 | Hassidov et al. | | |

OTHER PUBLICATIONS

Written Opinion for International Application No. PCT/IL2015/051077 filed Nov. 9, 2015, pp. 1-4.
International Preliminary Examination Report dated Jul. 27, 2016 for International Application No. PCT/IL2015/051077 filed Nov. 9, 2015, pp. 1-11.

* cited by examiner

HOLLOW PROBE WITH SLEEVE

FIELD OF THE INVENTION

The present invention relates generally to the propulsion of objects within a lumen, and specifically to methods and devices for propelling medical instruments through a colon.

BACKGROUND OF THE INVENTION

The use of an endoscope for examining a body cavity is well known in the art. The diagnostic and therapeutic advantages conferred by direct examination of the gastrointestinal tract with a flexible endoscope have made this method a standard procedure of modern medicine. One of the most common endoscopic procedures is a colonoscopy, which is performed for a wide variety of purposes, including: diagnosis of cancer, determination of the source of gastrointestinal bleeding, viewing a site affected by inflammatory bowel disease, removing polyps, and reducing volvulus and intussusception.

While colonoscopies are useful and effective procedures, they are difficult for a physician to perform. Colonoscopies can be painful and include risks to the patient's long term health. These problems stem from the need to push and steer a long, flexible colonoscope through the patient's intestine by pushing the colonoscope into the patient from the colonoscope's proximal side, located outside the patient's body.

It would therefore be desirable to provide a mechanism to facilitate insertion and extraction of an endoscope that lowers the risk of injury to the patient.

U.S. Pat. No. 4,615,331 to Kramman, entitled "Medical instruments with aid to introduction" disclose an elongated medical instrument for the examination or treatment of body cavities, in particular endoscopes, with a device to assist introduction by the principle of the tubular structure which becomes everted. The instrument includes a pipe 2 which is open at both ends and has pressure connectors 3 on the sides, and a flexible, eversible tubular structure 4 running through the pipe 2. The two ends 5, 6 of the tubular structure, each is connected to one end 7, 8 of the pipe 2, the medical instrument 9 runs through the pipe 2 inside the tubular structure 4, and the tubular structure 4 is folded in several double-layers in the region 10 of the distal end 11 of the medical instrument 9.

U.S. Pat. No. 6,702,735 to Kelly, entitled "Device for Movement Along a Passage" discloses a device for moving a tool along a passage, particularly for use in medical procedures, e.g. a colonoscope, which is surrounded by a sheath. The sheath has an inflatable region for engaging the passage wall, e.g. a colon. An annular extension region of the sheath is provided which becomes part of the inflated inflatable region, thereby increasing its length as the fluid pressure acts against a head of a tool to draw the tool along the passage. The annular extension region has sheath parts which face one another by their relative orientation caused by crumpling of the extension region, or the sheath parts are provided by folded portions. The extension region moves together with the tool as the sheath parts sequentially move into the inflated inflatable region. After inflation of the inflatable region of the sheath, inflation pressure acts against an inflatable head carried at the distal end region of the tool to draw the tool along the passage.

US Patent Application Publication No. 2008/0221390 to Konstantin, entitled "Medico-Technical Device Comprising a Self-Lubricating Element" discloses a technical medical device which can be engaged with a human or animal body while comprising a self-lubricating element, such as a an everting tube, that is subjected to internal friction in the device, wherein at least one surface of the self-lubricating element is plasma-treated.

SUMMARY OF THE INVENTION

It is an object of some aspects of the present invention to provide an improved system and method for propelling an object within a lumen.

It is a further object of some aspects of the present invention to provide an improved propulsion mechanism for advancing an endoscope within a body cavity of a patient for purposes of examination, diagnosis, and/or treatment of the patient.

There is thus provided, in accordance with an embodiment of the present invention, an endoscopic probe which advances within a lumen. The probe includes a central valve unit that features a central bore having a proximal end and a distal end, and at least one valve for controlling the introduction and withdrawal of fluid into the central bore. The probe further includes a sliding tubular sheath movably disposed inside the central valve unit, and a flexible sleeve, impermeable to the fluid and sealingly anchored to the central valve unit on both the distal and proximal ends. The sleeve is folded over to cover both the inside and outside of the sheath to sealingly envelop the sheath and contain the fluid, together with the valve unit, while allowing sliding of the sheath inside.

The at least one valve may be incorporated in the central valve unit, and may include a distal valve and a proximal valve. The probe may include a separating mechanism for blocking passage of fluid directly from the distal valve to the proximal valve.

A distal side of the sleeve may be inflated in order to propel the sheath forward within the lumen, while allowing deflation of the proximal side if required, and a proximal side of the sleeve side may be inflated in order to propel the probe backward within the lumen, while allowing deflation of the distal side, if required.

The sleeve may extend/expand beyond a distal edge of the sheath as the sheath advances forward, and extend/expand beyond a proximal edge of the sheath as the sheath recedes backward. The at least one valve may include a distal valve and a proximal valve, wherein the sleeve extends/expands beyond a distal edge of the sheath, as fluid is introduced into a distal portion of the sheath through the distal valve and the sheath advances forward, and wherein the sleeve extends/expands beyond a proximal edge of the sheath, as fluid is introduced into a proximal portion of the sheath through the proximal valve and the sheath recedes backward. The fluid may include gas, pressurized gas, or liquid.

A portion of the sleeve may include a variable diameter to accommodate variable lumen. The sleeve may include anesthetic (or other medical substances such as markers) coating or deposit laid over its internal face, which comes in contact with the human colon.

The probe may further include a pushing and/or pulling mechanism used to push or pull the sleeve inside the sheath. The probe may include a propulsion mechanism for sliding the sheath inside the probe, wherein the mechanism includes at least one of: a sprocket wheel, a toothed mechanism, a friction based mechanism, an indented sleeve, a perforated sheath, a slotted sheath, an externally serrated/indented sheath, and an internally serrated/indented sheath.

The probe may further include a rod which can be selectively inserted within the central bore of the sheath, the rod may include at least one of: a bulbous head for facilitating push/pull of the sheath, an expandable head for facilitating push/pull of the sheath, an expandable head for selectively blocking fluid flow inside the sleeve at a blocking location disposed within the bore of the sheath, and an instrument for examination, diagnosis and treatment of the patient.

The probe may further include a sleeve pulling wire for assisting retraction of the sleeve from the sheath, and sheath pulling wires for sheath tip angulation and steering, as well as inchworm motors for pulling the sheath pulling wires.

The probe may further include instruments for examination, diagnosis and treatment of the patient, disposed within the central bore of the sheath outside the sleeve, within the central bore of the sheath within the sleeve, when inserted between the sheath and the sleeve, embedded in the sheath, deployed beside the sheath within the sleeve, or deployed beside the sheath outside the sleeve.

In accordance with another aspect of the present invention, there is thus provided, a method for propelling an endoscopic probe within a lumen, including inserting a flexible sleeve within a tubular sheath, sliding the sheath through a central bore of a central valve unit, folding over a proximal sleeve portion and a distal sleeve portion of the sleeve inside out over both ends of the sheath to cover both the inside of the sheath and the outside of a proximal sheath portion and a distal sheath portion of the sheath, sealingly anchoring the proximal sleeve portion to a proximal bore end of the central bore and the distal sleeve portion to a distal bore end of the central bore, such that the sleeve together with the valve unit sealingly envelop the sheath, inserting a distal tip portion of the sleeve-covered sheath into the lumen, and advancing and retracting the sheath within the lumen while maintaining the sheath covered by the sleeve.

The central valve unit may include at least one valve for controlling the introduction and withdrawal of a fluid into the central bore and wherein the sleeve may be impermeable to the fluid, such that the sleeve, together with the valve unit, sealingly contain the fluid. The fluid may be gas, pressurized gas, or liquid.

The method may further include inflating at least a portion of the sleeve with the fluid, through the at least one valve when advancing or retracting the sheath within the lumen. The method may further include inflating a distal side of the sleeve using the central valve unit to insert the probe, and a proximal side of the sleeve to extract the probe. The method may further include extending/expanding the sleeve beyond a distal edge of the sheath when advancing the sheath forwards, and extending/expanding the sleeve beyond a proximal edge of the sheath when receding the sheath backwards. The at least one valve may include a distal valve and a proximal valve, and method may further include extending/expanding the sleeve beyond a distal edge of the sheath, as introducing fluid into a distal portion of the sheath through the distal valve and the sheath advances forward, and extending/expanding the sleeve beyond a proximal edge of the sheath, as introducing fluid into a proximal portion of the sheath through the proximal valve and the sheath advances backward.

The method may further include blocking by a separating mechanism the passage of fluid directly from the distal valve to the proximal valve. A portion of the sleeve may include a variable diameter to accommodate variable lumen. The method may further include coating/depositing a face of the sleeve with an anesthetic or other medical substance. The method may further include pushing and/or pulling the sleeve inside the sheath for pushing and/or pulling the sheath inside the lumen. The method may further include sliding the probe by a propulsion mechanism, wherein the mechanism may include a sprocket wheel, a toothed mechanism, a friction based mechanism, an indented sleeve, a perforated sheath, a slotted sheath, an externally serrated/indented sheath, or an internally serrated/indented sheath.

The method may further include selectively inserting a rod within the central bore of the sheath, wherein the rod may include a bulbous head for facilitating push/pull of the sheath, an expandable head for facilitating push/pull of the sheath, an expandable head for selectively blocking fluid flow inside the sleeve at a blocking location disposed within the bore of the sheath, or an instrument for examination, diagnosis and treatment of the patient.

The method may further include retracting the sleeve from the sheath by a pulling wire. The method may further include sheath tip angulating and steering by sheath pulling wires, which may be pulled by inchworm motors.

The method may further include disposing instruments for examination, diagnosis and treatment of the patient within the central bore of the sheath outside the sleeve, within the central bore of the sheath within the sleeve, inserted between the sheath and the sleeve, embedded in the sheath, deployed beside the sheath within the sleeve, or beside the sheath outside the sleeve.

BRIEF DESCRIPTION OF THE DRAWINGS

The present invention will be understood and appreciated more fully from the following detailed description taken in conjunction with the drawings in which.

DETAILED DESCRIPTION OF THE EMBODIMENTS

Figure 1:
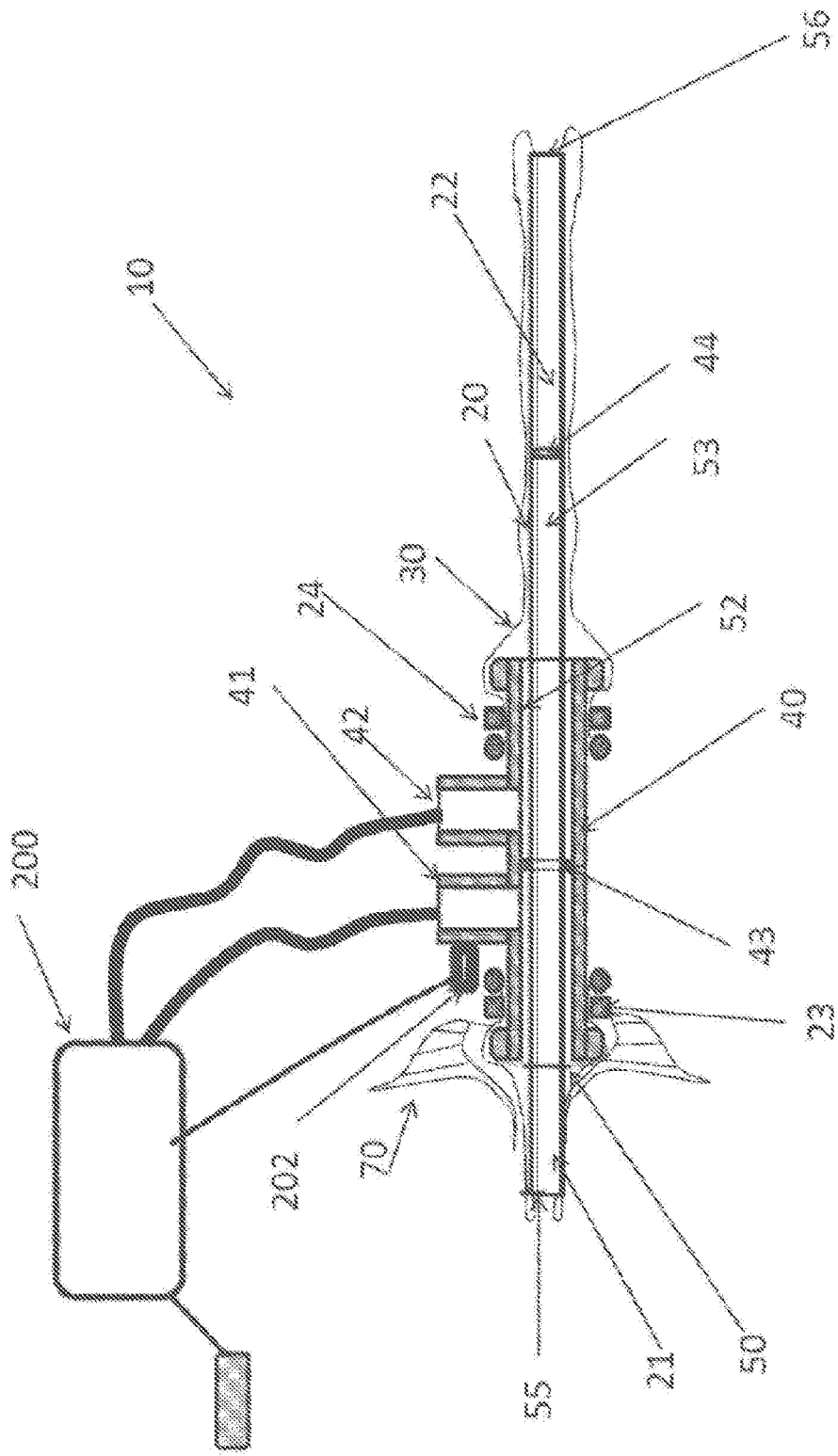
FIG. 1 is a schematic, cross-sectional illustration of an embodiment of a dual-valves endoscopic probe with flexible sleeve, constructed and operative in accordance with the invention.

In preferred embodiments of the present invention, a hollow probe is advanced through the lower gastrointestinal tract of a patient, by optionally inflating a flexible sleeve coupled to the probe. The probe includes a tubular sheath, and the flexible sleeve is inserted within the sheath and inverted over the sheath tips to envelop the sheath when wrapping both the external and the internal faces of the sheath. Both ends of the sleeve are anchored, at intermediate locations around the sheath to an external central valve unit, typically disposed adjacent to the patient's anus during operation. The sleeve, together with the valve unit, sealingly envelop the sheath. In other words, the central valve unit encircles the sheath at some intermediate portion thereof, and the anchored sleeve externally enshrouds the other sheath portions (proximal and distal), and enfolds internally to envelop the entire internal tubular cavity of the sheath, while leaving an internal passage within the sleeve allowing insertion of medical examination, diagnosis and treatment equipment there through. The sleeve is impermeable to a fluid that can be introduced there into through the valve unit. The sleeve, together with the valve unit, sealingly envelop the sheath and contain the introduced fluid, while allowing sliding of the sheath. As the sleeve is inflated by the fluid, preferably using gas, pressurized gas (including air) or liquid, the probe is propelled forward. Simultaneously or alternatively, the sheath can be pushed manually on its proximal side, or by some mechanized propulsion. Optionally, is no liquid is introduced into the sleeve (by the choice of the operator or if no liquid supply is available), the arrangement of the sheath within a sleeve can still be fully operational (e.g. by letting free flow of ambient air into the sleeve through the valve unit), requiring conventional push and pull action of the sleeve-covered-sheath within the lumen, while the sleeve retains its protective no-rubbing characteristic as it is not sliding against the wall of the lumen due to its anchoring to the valve unit. The inflation of the flexible sleeve can be controlled, so that the sleeve is fed out of the sheath gradually. A portion of the sleeve that is inflated expands radially outward and remains substantially stationary relative to the intestinal wall as long as the sleeve is inflated, without rubbing the intestinal wall, avoiding frictional damage thereto and facilitating frictionless movement within the gastrointestinal tract. The probe can thereby be advanced or retracted (inserted and extracted) more easily, and trauma to the gastrointestinal tract is minimized.

The flexible sleeve can be pushed forward by a push-pull rod, or pulled back by an extra wire connected to the flexible sleeve, or with the application or mechanical propulsion.

The central bore of the probe can include separate steering for easing the maneuvering of the probe over or around curves in the gastrointestinal tract and obstructions, such as, blood clots, small deformations and other obstacles, so that the probe can move within the patient's body while further minimizing harmful contact and friction. Any suitable steering methods known in the art may be used.

The probe's central bore can also accommodate instruments for examination, diagnosis and treatment of the patient, and such instruments may also be embedded in the sheath or inserted beside the probe—between the sheath and the sleeve or on the sleeve. Preferably, the instruments include an endoscopic instrument—an imaging device, such as, a miniature video camera and light source, as are known in the art, which are used to capture endoscopic images, and therefore the terms "probe" and "endoscopic probe" are interchangeably used herein. Accessories for operating the instruments and receiving data therefrom can include wires, fiber-optic lines, or tubes which are coupled to the instruments and extend to an operator or to equipment outside of the patient, which operates the instruments and receives or transmits data therefrom. The wires, line or tubes preferably pass through the central bore of the probe and out through the central valve unit. Wireless instruments may also be used.

Figure 7:
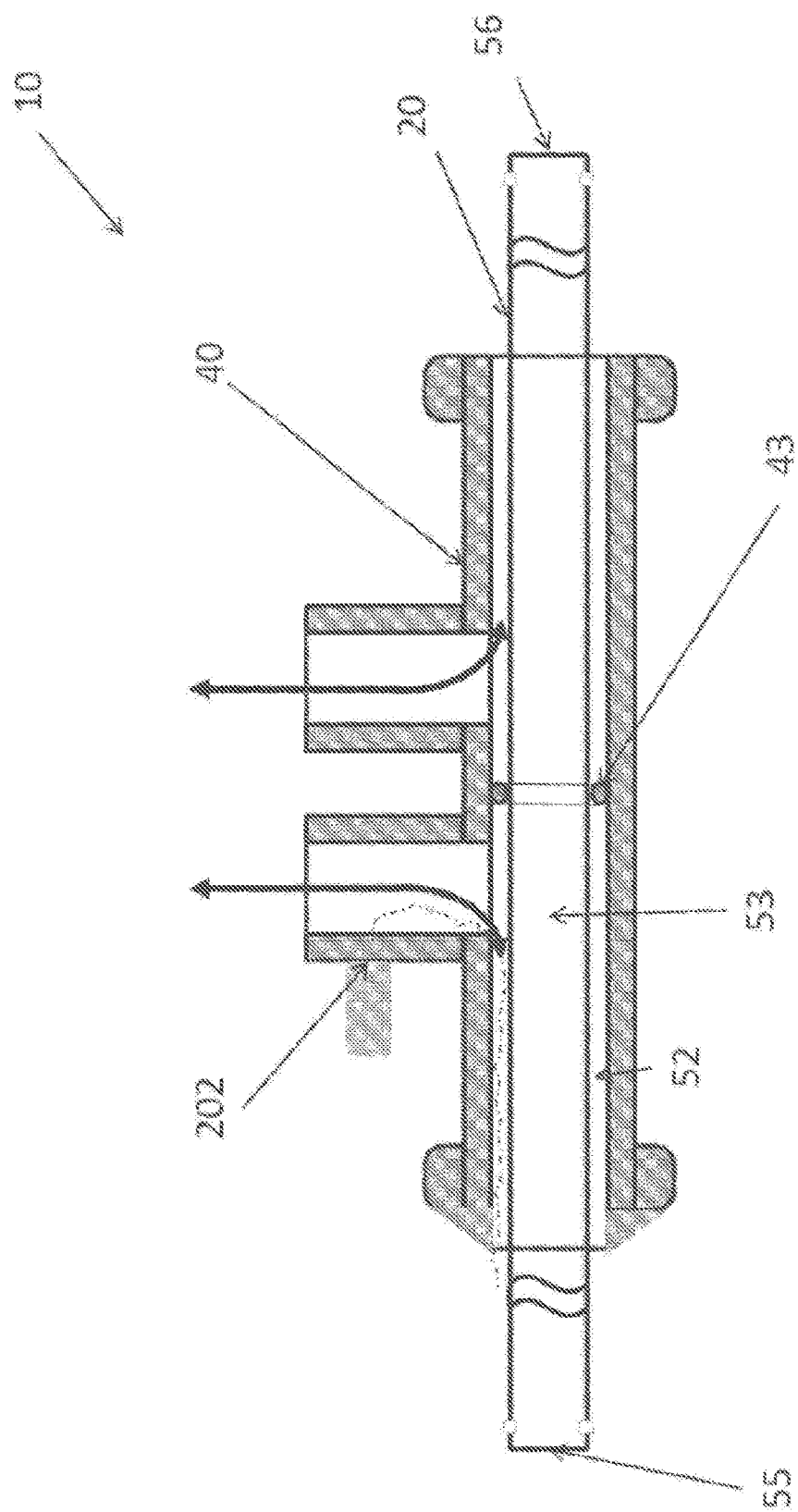
FIG. 7 is a schematic, cross-sectional illustration of an embodiment of a central valve unit featuring dual valves configured for the embodiment of FIG. 1.

Reference is now made to the Figures, in which like numbers designate like parts. FIG. 1 is a schematic, cross-sectional illustration of an embodiment of a dual-valves endoscopic probe 10 with flexible sleeve, constructed and operative in accordance with the invention. Reference is also made to FIG. 7, which is a schematic, cross-sectional illustration of central valve unit 40 featuring dual valves configured for probe 10. Probe 10 includes a central valve unit 40. The distal end 50 of central valve unit 40 is connected to anus adaptor 70. Probe 10 also includes flexible sheath 20 that is configured to slide within central bore 52 of central valve unit 40. Sheath 20 preferably has a hollow tubular shape, with an external diameter which is smaller than the diameter of interior bore 52 of central valve unit 40, allowing free slide movement of sheath 20 within bore 52. Sheath 20 has a central bore or tubular cavity 53. Optionally, insertion and accommodation of instruments for examination, diagnosis and treatment of the patient can be within bore 52, and in some instances, also within bore 53. Probe 10 further includes sleeve 30 which is preferably made from a flexible, biocompatible plastic material, of any suitable type known in the art, and is further preferably impermeable to fluids that may be contained therein. Sleeve 30 preferably has a wall thickness between approximately 0.1 and 0.4 mm and an overall diameter of approximately 15 mm when inflated. Sleeve 30 is inserted within and along tubular cavity 53, and is folded over sheath 20 at tips 55, 56 of sheath 20, and thereby inverted to cover distal portion 21, and proximal portion 22 of sheath 20, and is sealingly and tightly fastened to both sides of central valve unit 40 by anchorings 23 and 24. Sleeve 30, together with valve unit 40 sealingly envelop sheath 20, which is completely enshrouded by sleeve 30 and valve unit 40, with its central tubular cavity 53 left open for insertion and accommodation of tools and instruments for examination, diagnosis and treatment of the patient there through, while the instruments are maintained isolated from the internal face of sheath 20 (namely, the wall of sheath tubular cavity 53) by sleeve 30.

The central hollow bore 53 of probe 10 (the interiors of central valve unit 40 and sheath 20) enables the insertion and extraction of medical treatment or diagnostic tools, and/or other mechanisms within the interior of probe 10, e.g., mechanisms used for easing the movement of sleeve 30 within sheath 20.

Sleeve 30 typically has an unfolded length of approximately 3 meters. Sheath 20 typically has a length of approximately 1.5 meters. Sleeve 30 can be folded in a way so that the length of folded sleeve 30 is still greater than the length of sheath 20.

Preferably, probe 10 includes a steering capabilities, which can be included as part of a diagnostic tool. The steering capabilities can include steering mechanisms, as are known in the endoscopic art, such as, mechanisms that rely on the use of pull-wires for steering. Examples of such steering units are described herein below with reference to FIGS. 17 and 18.

Central valve unit 40 enables the controlled intake and outtake of a fluid, liquid or gas, into the interior volume of folded sleeve 30, keeping sheath 20 totally immersed in the fluid.

Forward illumination 202, including wiring as in FIG. 7, may be inserted between sheath 20 and bore 52 for facilitating inspection around distal edge 55 of distal portion 21 of sheath 20 when inserted within colon 101 of human body 100, and sleeve 30 (and sheath 20, if required) may be sufficiently transparent to allow illumination therethrough. In this context it is noted that tools, sensors and/or instruments for examination, diagnosis and treatment of the patient may be disposed in least one of a variety of locations, including within central bore 53 of sheath 20 outside sleeve 30, within central bore 53 of sheath 20 within sleeve 30 (inserted between sheath 20 and sleeve 30), embedded in sheath 30 as exemplified in FIG. 16, deployed beside sheath 20 within sleeve 30 (inserted between sheath 20 and sleeve 30) as exemplified by forward illumination 202 in FIGS. 7, 10, 11, 13 and 14, and deployed beside sheath 20 outside sleeve 30.

Figure 2:
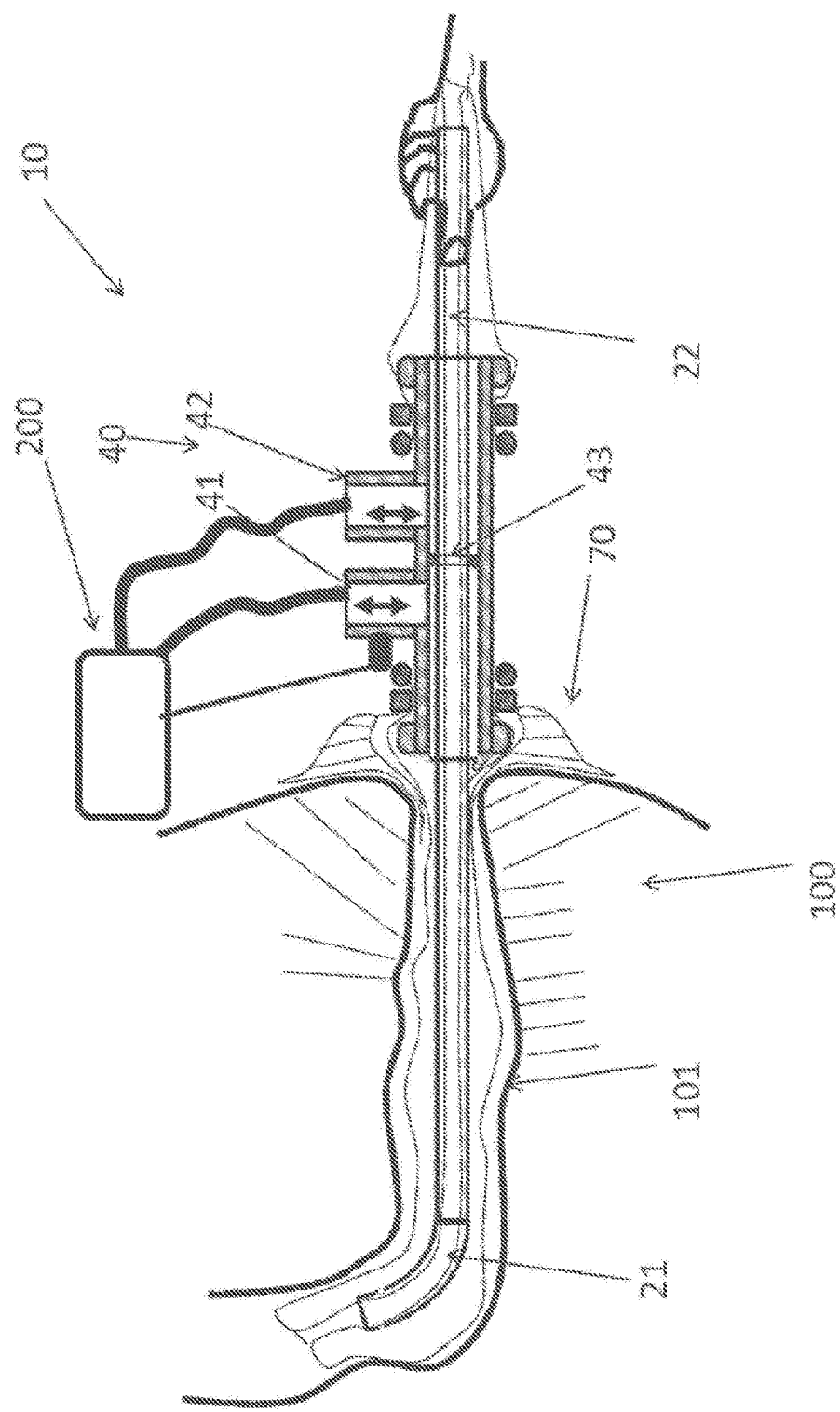
FIG. 2 is a schematic, cross-sectional illustration of the probe of FIG. 1 while inserted in a patient's body.

Reference is now made also to FIG. 2. FIG. 2 is a schematic, cross-sectional illustration of probe 10 being used in an endoscopic examination of a patient's colon 101, while inserted in a patient's body 100. Probe 10 is inserted into colon 101 through the patient's anus. A liquid or gas fluid pump/supplier 200 is then actuated by opening the relevant valve, for example distal valve 41 or proximal valve 42, depending on whether insertion or extraction is desired. When insertion is desired, fluid is pumped through valve 41 into the distal portion of sleeve 30 covering sheath 20. Pump/supplier 200 is coupled to a source of liquid, or a regulated, pressurized source of gas, such as, carbon dioxide ($CO_2$) or any other suitable gas. Preferably, a gas pressure in the range of approximately 0.3 ATM is used to inflate sleeve 30. Alternatively, a liquid, such as sterile water, may be used to inflate sleeve 30. The inflated portion of sleeve 30 typically expands radially and may contact the interior wall of colon 101, but there is generally only minimal or no longitudinal motion of sleeve 30 against the wall of colon 101. Thus, rubbing and trauma to the intestinal wall are minimized. The expansion of the inflated portion of sleeve 30 pulls its internally inserted part within bore 53 of sheath 20 at the expense of the remainder of sleeve 30 about the proximal portion 22 of sheath 20, thereby the mere shortening of the proximal part of sleeve 30 can be used to push sheath 20 further into human colon 101. During such insertion procedure into human colon 101, the fluid within proximal portion of flexible sleeve 30 covering proximal portion 22 is allowed to withdraw through valve 42), to nullify excess fluid resistance.

Figure 3:
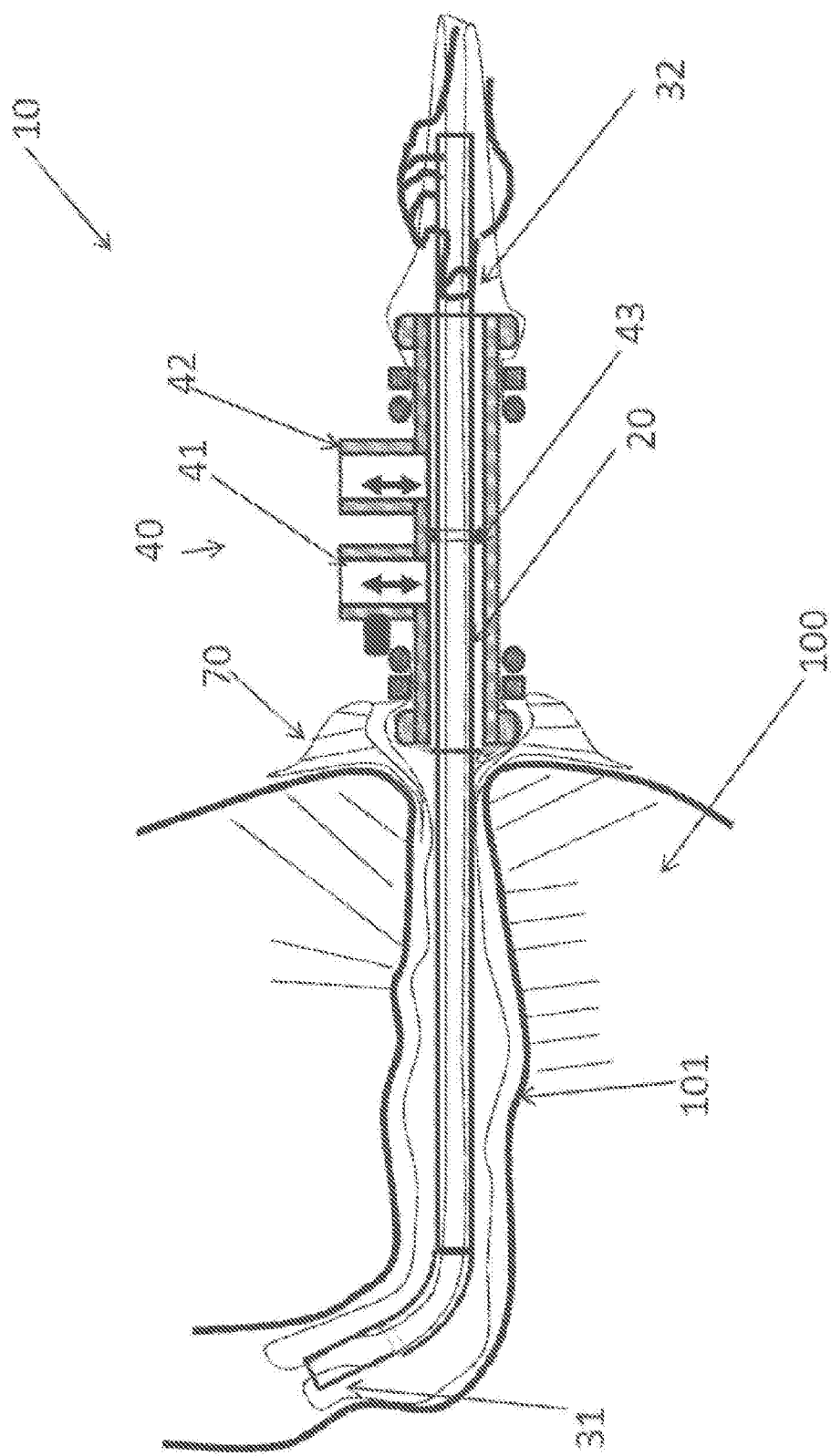
FIG. 3 is a schematic, cross-sectional illustration of the probe of FIG. 2 with its sheath inserted further into the patient's body.

Reference is now made also to FIG. 3, which is a schematic, cross-sectional illustration of the probe 10 with sheath 20 inserted further into the patient's body (colon 101) to advance probe 10 further along the interior of colon 101, a distal part 31 of sleeve 30 is inflated by opening valve 41 and pushing a liquid or gas through it into the interior of sleeve 30. as a result, the distal part 31 of sleeve 30 will extend/expand beyond the distal edge of sheath 20 into and against the interior wall of colon 101. sheath 20 can then be manually pushed toward distal part 31 of sleeve 30. the configuration of a long sleeve squeezed along sheath, typically results in minimal or completely nil fluid passage between sheath internal side (bore 53) and sleeve 30 that passes inside bore 53, because of the pressure of the endoscopic probe, or the pressure of another instrument that squeeze them together, or because sleeve 30 is tightly folded over the sheath ends 55, and 56. Simultaneously to the manual pushing of sheath 20, a pedal can be actuated in order to supply additional liquid or gas to distal part 31 of sleeve 30 in order to further push and advance sleeve 30 along the interior of colon 101. At the same time the liquid or gas that is present or has leaked back to the proximal end of the sleeve through a separating mechanism, such as, separation O-ring 43, that is utilized to block the flow or passage of fluid directly from valve 41 to valve 42, (allowing passage only past edges 55 and 56, and along the entire length of sleeve 30 within bore 53, if it is possible) can be extracted from proximal part 32 of sleeve 30 (through valve 42). Similarly, an optional internal separating blocking element 44 (which can also feature an O-ring) can be placed, selectively or throughout the entire session, anywhere within bore 53 to press sleeve 30 against the internal face of bore 53 and thus hermetically block passage of fluid past edges 55 and 56, and along the entire length of sleeve 30 within bore 53, if such a passage is not blocked anyways as noted above. Element 44 can be integral with sleeve 30. Element 43 alone (in case passage of fluid within and between sleeve 30 and bore 53 is insignificant or not possible), or the two blocking element, 43 and 44 (as much as element 44 is required to block passage of fluid within and between sleeve 30 and bore 53), create two completely isolated pockets which can be separately inflated and deflated, using the two distinct valves, 41 and 42. Advance of sleeve 30 inside sheath 20 toward the distal edge of sheath 20 can be supported by a suitable mechanism, such as, a push-pull rod, alone or combined with medical instrumentation (described below with reference to FIGS. 4 and 9).

In order to avoid perforation of sleeve 20, particularly at its distal side 31, a diagnostic tool, which can be included as part of or separate from the push-pull rod, is used to monitor the distance between distal edge 55 of sheath 20 and distal part 31 of sleeve 30.

To retract probe 10 from colon 101, the proximal part 32 of sleeve 30 is inflated by opening valve 42 and pushing liquid or gas through it into the interior of sleeve 30. At the same time, the liquid or gas can be extracted from distal part 21 of sleeve 30 through valve 41, causing sleeve 30 to expand/extend beyond the proximal edge 56 of sheath 20. A portion of sleeve 30 can then be manually folded over the proximal edge of sheath 20. Sheath 20 is then extracted from colon 101 by pulling manually on sheath 20 away from distal part 21 of sleeve 30.

Simultaneously to the manual pulling of sheath 20, a pedal can be actuated in order to supply additional liquid or gas to proximal part 32 of sleeve 30 in order to further push and advance sleeve 30. At the same time, the liquid or gas that is present in, or has leaked from proximal part 32 to the distal part 31, can be extracted from distal part 31 of sleeve 30 (through valve 41).

After an endoscopic examination is complete, the pressure in sleeve 30 can be relieved, and sleeve 30 deflated, for a relatively quick retraction of probe 10. In this case probe 10 can be withdrawn from colon 101 by pulling on sheath 20.

Probe 10 can feature a rod, which can be selectively inserted within the central bore of sheath 20. The rod may be used for various purposes. The rod may include at least one of: bulbous head for facilitating push/pull of sleeve 30, expandable head for facilitating push/pull of sleeve 30, expandable head for selectively blocking fluid flow in sleeve 30 at a blocking location disposed within bore 53 of sheath 20 (functioning as blocking element 44), and instruments used for examination, diagnosis and treatment of the patient.

Figure 4:
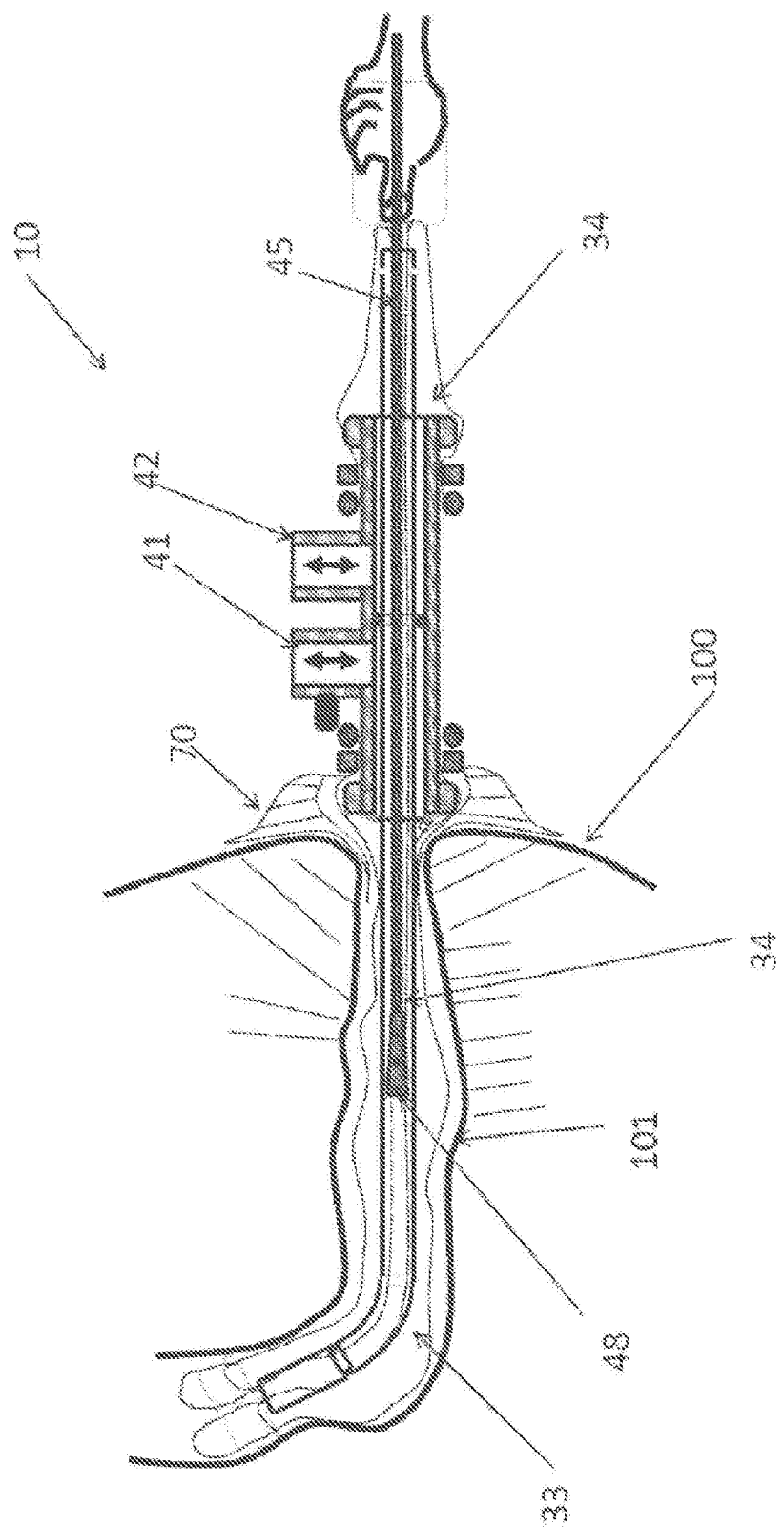
FIG. 4 is a schematic, cross-sectional illustration of the probe of FIG. 3 with a push-pull rod for assisting insertion and/or extraction of the probe.
Figure 9:
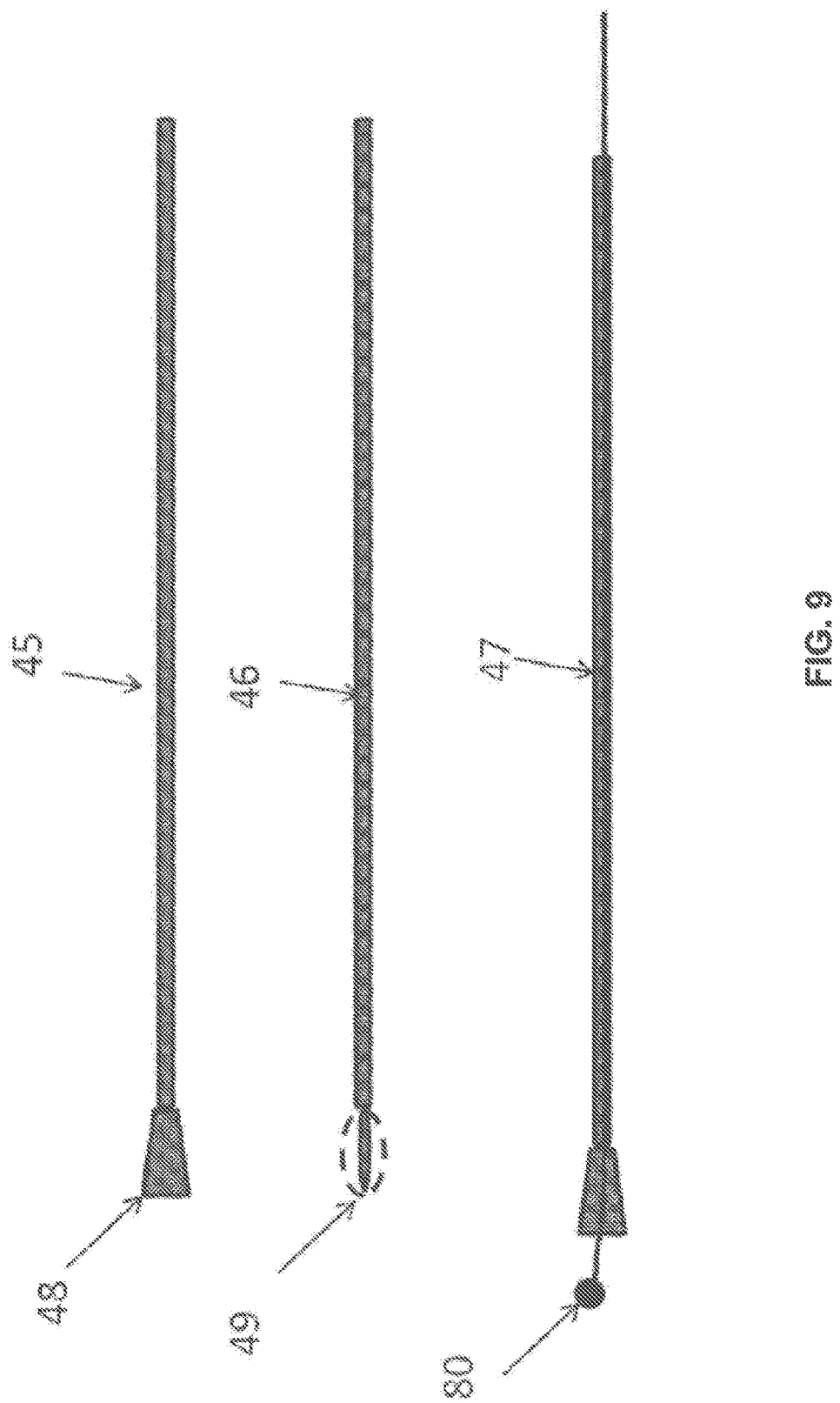
FIG. 9 includes schematic illustrations of embodiments a push-pull rod, a push-pull rod with inflatable and deflatable head, and a combination push-pull rod/diagnostic tool configured for operation in conjunction with an endoscopic probe with flexible sleeve, constructed and operative in accordance with the invention.

FIG. 4, Is a schematic, cross-sectional illustration of probe 10 illustrating a steering mechanism for assisting insertion and/or extraction of probe 10, such as, a push-pull rod 45, used to advance sleeve 30 inside sheath 20 toward the distal edge of sheath 20 during insertion or toward the proximal edge of sheath 20 during extraction. A portion, preferably head 48, of push-pull rod 45 can be sized with a diameter that will cause push-pull rod 45 to put sleeve 30 in contact with sheath 20. This contact can seal a portion of sleeve 30 against sheath 20 to create fluid seal separating the volume contained within sleeve 30 in to two pockets: a proximal pocket 34 and a distal pocket 33, and prevent the passage of air from one section of sleeve 30 (pocket 33) to another (pocket 34) (pockets 33, 34 overlap sides 31, 32, correspondingly, but may also extend to partially occupy the other side—such as pocket 34 extending from side 32 toward side 31, depending on the location of head 48). This can assist a user to control which sections of sleeve 30 are inflated. Push-pull rod 45 can include a mechanism for adjusting the size of a portion of its diameter, such as an inflatable and deflatable head 48. Reference is now made also to FIG. 9. FIG. 9 includes schematic illustration of embodiments of push-pull rod 45 with head 48, push-pull rod 46 with inflatable and deflatable head 49, and a combination push-pull rod/diagnostic tool 47 configured for operation in conjunction with an endoscopic probe with flexible sleeve, constructed and operative in accordance with the invention. Push-pull rod 45 includes head 48, and push-pull rod 46 includes inflatable head 49 that help facilitate the pushing and pulling of sleeve 30 inside sheath 20. Pushing and pulling of push-pull rod 45 or 46 can be synchronized with the inflation and deflation of inflatable head 48. The inflation of head 49 within sheath 20 can be progressed to the extent of sealingly clasping the inner portion of sleeve 30 within bore 53 to the inner face of sheath 30 and prevent passage of fluid through sleeve 30 at this sealing location. Push-pull rod 47 combines a diagnostic tool 80 (similar to diagnostic tool 80 of FIG. 5) and a push-pull rod (similar to push-pull rod 45) to provide a combination of a diagnostic tool and a push-pull rod.

Figure 5:
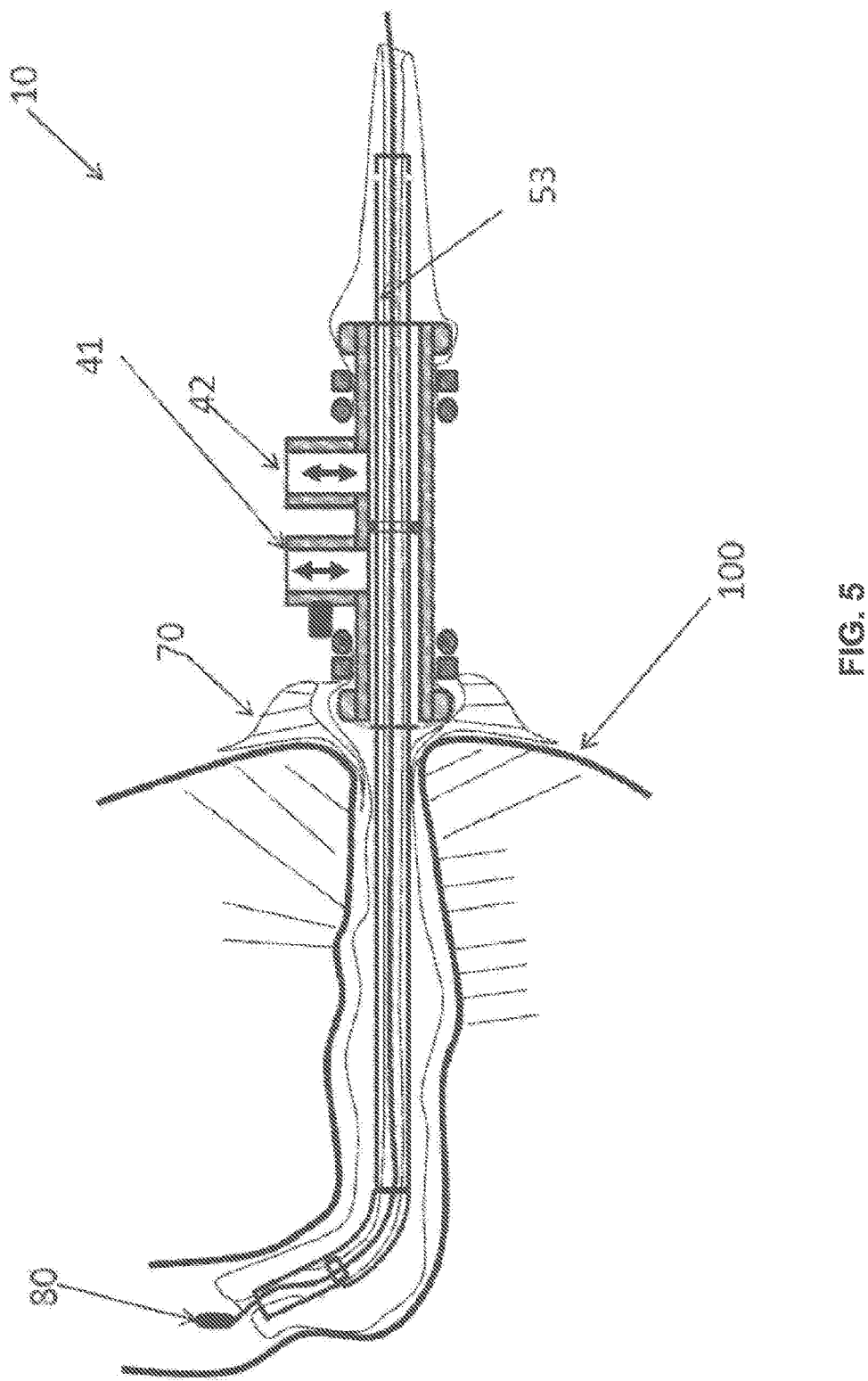
FIG. 5 is a schematic, cross-sectional illustration of the probe of FIG. 3 with a diagnostic tool inserted in the central bore of the probe.

FIG. 5, is a schematic, cross-sectional illustration of probe 10 illustrating a diagnostic tool 80 inserted in the central bore 53 of sheath 20 and probe 10. While inserting treatment or diagnostic tool 80 through the central bore 53, sleeve 30 can be deflated to ease the insertion of the tool 80 (e.g. by extracting any excess fluid, liquid or gas, remaining in the interior of sleeve 30 through valve 41 and/or 42). Deflation of sleeve 30 may involve complete extraction of fluid therefrom to the extent sleeve 30 is tightly adhered by the internal vacuum created within sleeve 30 to both sides of sheath 20, rendering both into an overtube-like configuration (sleeve 30-"coated" sheath 20). Such a configuration leaves the widest possible clear passage within bore 53 for convenient insertions and retractions of diagnostic tools or instruments, such as used, for instance, in polyp removal surgery.

It is noted that when sleeve 30 is inflated and is advanced or retracted in conjunction with, or for the sake of, advancing or receding sheath 20 within colon 101, the portion of sleeve 30 disposed within bore 53 advances/retracts twice the length sheath 20 advances/recedes, and is typically clenched inwardly about the central axis of bore 53. As a result, any object inserted through sleeve 30, such as tool 80 in FIG. 5 (particularly its cable or rod), or rod 45 in FIG. 4, is firmly grasped by the inflated, inwardly clenching, sleeve 30, which typically grasps and carries the inserted object twice the length by which sheath 20 progresses (to either direction). Accordingly, to avoid over-progression of the inserted object, sleeve 30 can be deflated, intermittently—if required, for allowing an offsetting reverse push or pull of the inserted object within bore 53, compensating for its already-occurred or prospective over-progression.

Diagnostic tool 80 can also include: suction and/or irrigation ports, sensors of various types and/or specially adapted surgical instruments, such as, biopsy forceps. These elements are known generally in the art, and are not shown in the figures. Substantially any other suitable type of tool or sensor may be adapted with tool 80 and coupled to an external apparatus by the appropriate adaptation of its cable (or rod) to the central bore 53 of probe 10.

Figure 6:
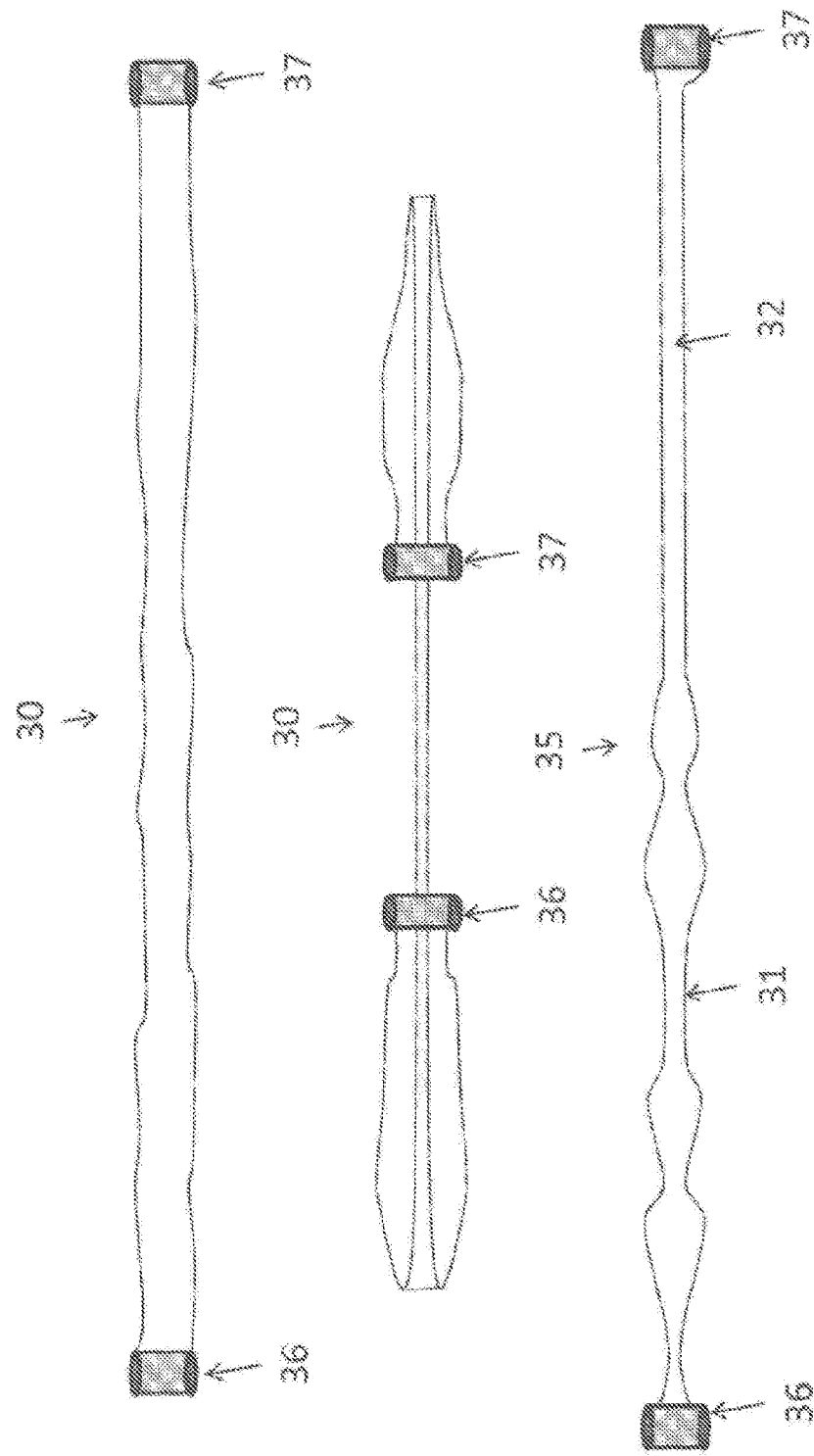
FIG. 6 includes schematic illustrations of embodiments of a flexible sleeve in folded and un-folded modes, and a variable diameter flexible sleeve, constructed and operative in accordance with the invention.

FIG. 6 includes schematic illustrations of embodiments of flexible sleeve 30 in folded and un-folded modes, and variable diameter flexible sleeve 35, constructed and operative in accordance with the invention. In certain embodiments, sleeves 30, 35 can have different properties or characteristics for different parts of the sleeve. For example, the (plastic or nylon) material on one or both ends 36, 37 of sleeve 30 can be thinner or thicker than other portions of the sleeve. The sleeve can also feature varying diameters on one or more portion of the sleeve. Sleeve 35, has a variable diameter on its distal side 31, that matches variations in the colon, and a fixed diameter that matches the sheath's (outer, or both outer and inner) diameter on its proximal side 32 (the side that does not reach the colon).

Figure 8:
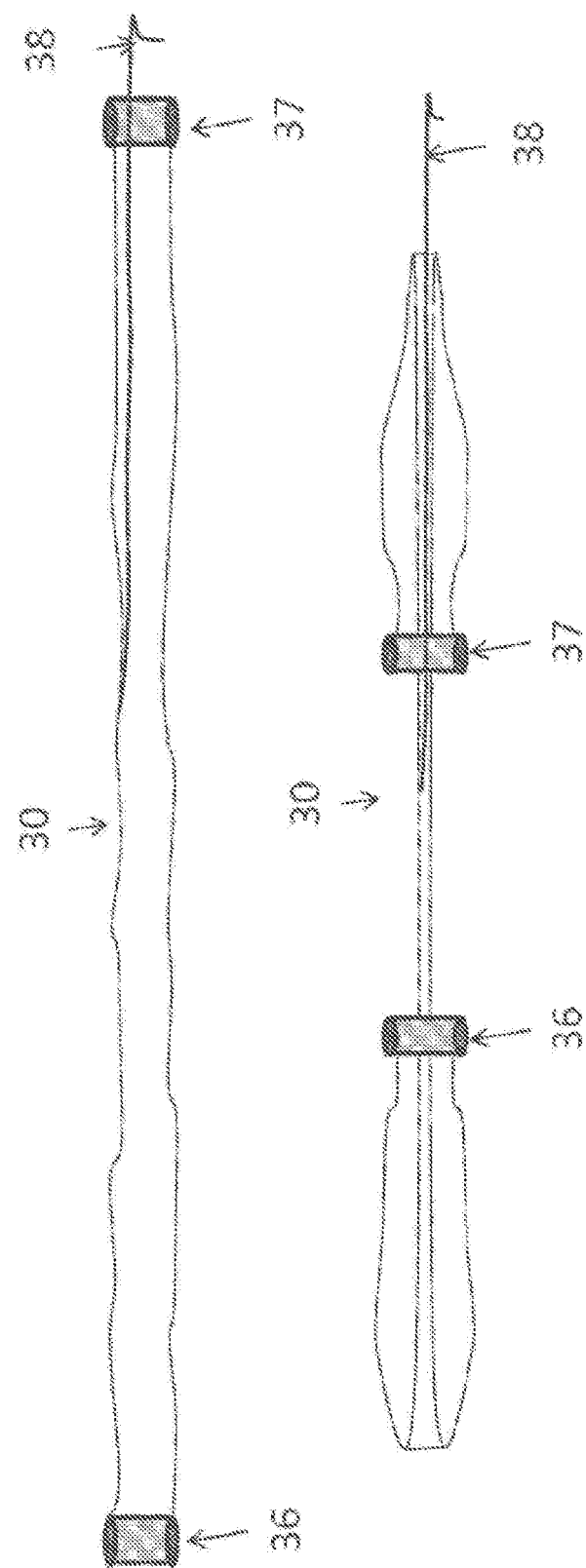
FIG. 8 includes schematic illustrations of an embodiment of a flexible sleeve constructed and operative in accordance with the invention with puling wire for assisting retraction of the sleeve.
Figure 10:
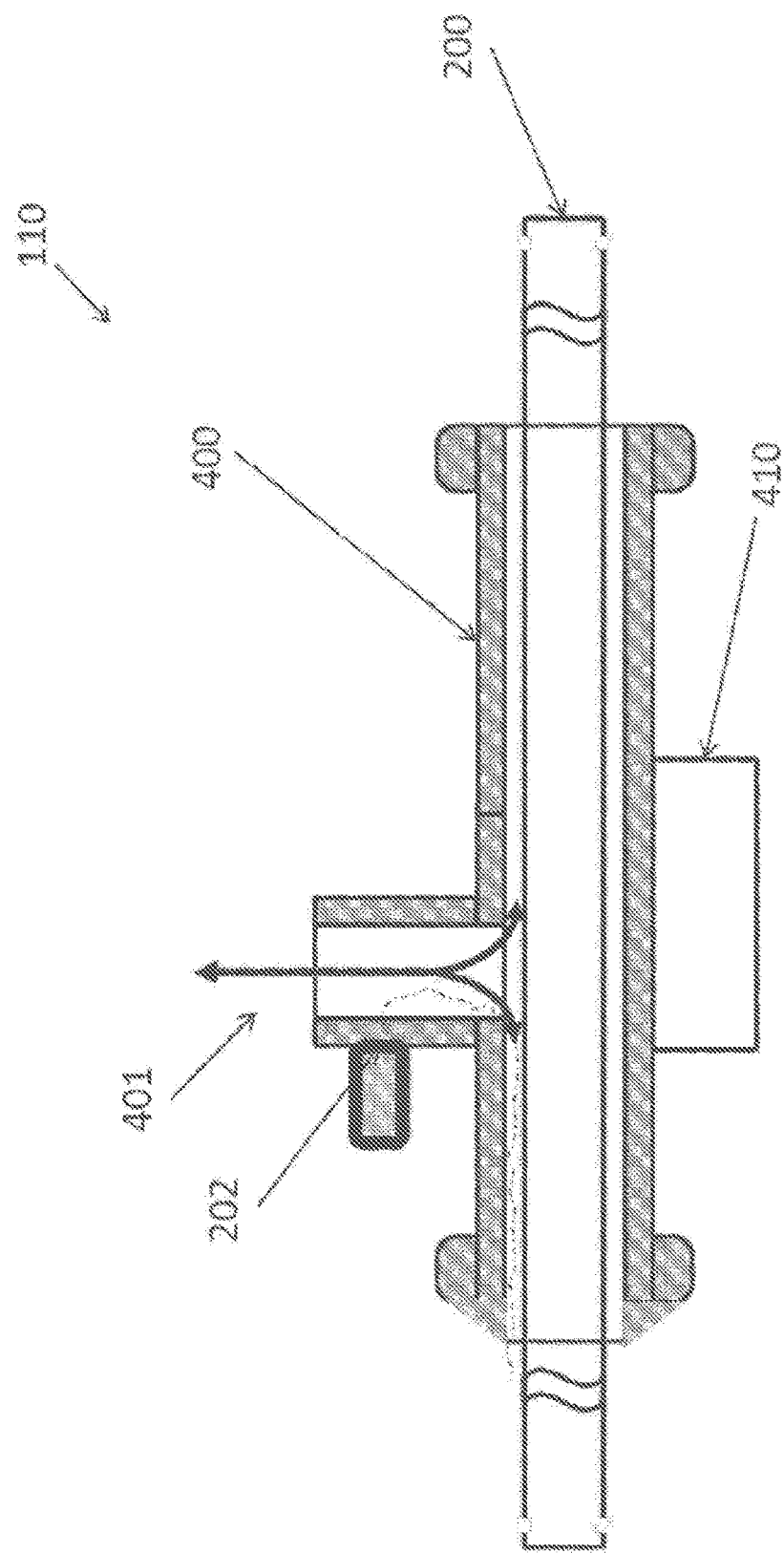
FIG. 10 is a schematic, cross-sectional illustration of an embodiment of a single-valve endoscopic probe, constructed and operative in accordance with the invention.

FIG. 8 includes schematic illustrations of an embodiment of flexible sleeve 30 constructed and operative in accordance with the invention with puling wire 38 for assisting retraction of sleeve 30. When sleeve 30 is require to be retracted within sheath 20, pulling wire 38 can be used to advance sleeve 30 inside sheath 20 towards proximal edge of sheath 20 by pulling on wire 38. FIG. 10 is a schematic, cross-sectional illustration of an embodiment of single-valve endoscopic probe 110, constructed and operative in accordance with the invention. Probe 110 is similar to probe 10 of FIG. 1, wherein single-valve unit 400 is applied instead of the dual valve unit 40. Single valve unit 400, includes valve 401 and allows filling or withdrawal of fluid from sleeve 30 in its entirety, without discriminating between the distal or proximal portions of sleeve 30. Accordingly, the advancement or retreat of sheath 20 within colon 101 is not performed with the aid of selective filling with fluid of the relevant portion of sleeve 30, and the sheath propulsion is either completely manual or conducted by further propulsion by unit 410

Figure 11:
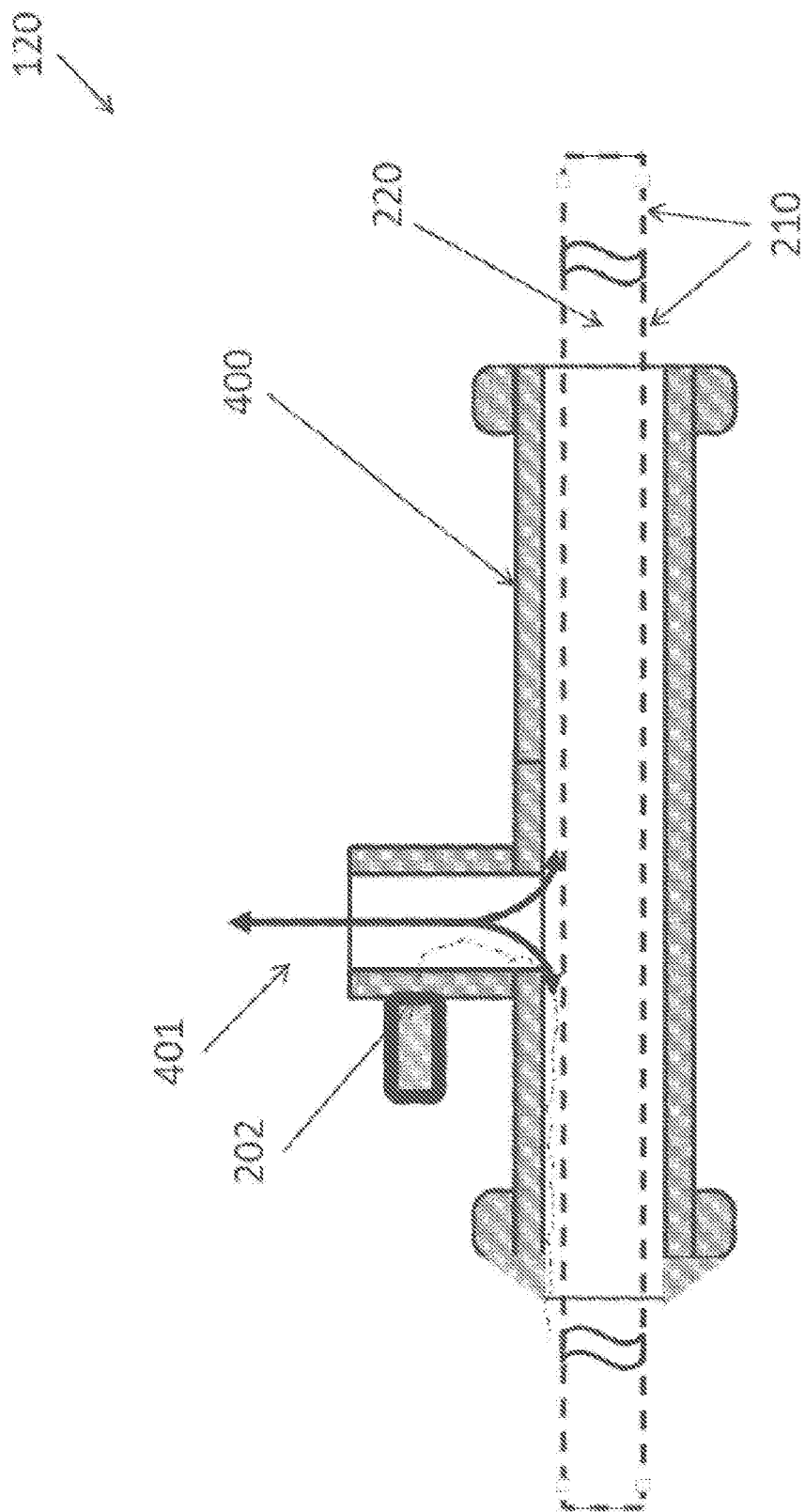
FIG. 11 is a schematic, cross-sectional illustration of an embodiment of a single-valve endoscopic probe, constructed and operative in accordance with the invention, featuring a perforated sheath.

FIG. 11 is a schematic, cross-sectional illustration of single-valve endoscopic probe 120, constructed and operative in accordance with the invention, featuring perforated sheath 220 (the sleeve is not shown). The perforation of sheath 220, represented by holes 210, allows easy passage of fluid, liquid or gas, within the sleeve through holes 210, allowing an almost uninterrupted flow within the sleeve, despite the obstruction of sheath 220 to a uniform, omnidirectional flow of fluid within the sleeve, for fast inflating and deflating of the sleeve.

Although shown with the single-valve unit 400 (and without the sleeve), the alternative sheaths and sleeves of FIGS. 11-14 can be utilized with the dual-valve unit 40 of FIG. 1.

Figure 13:
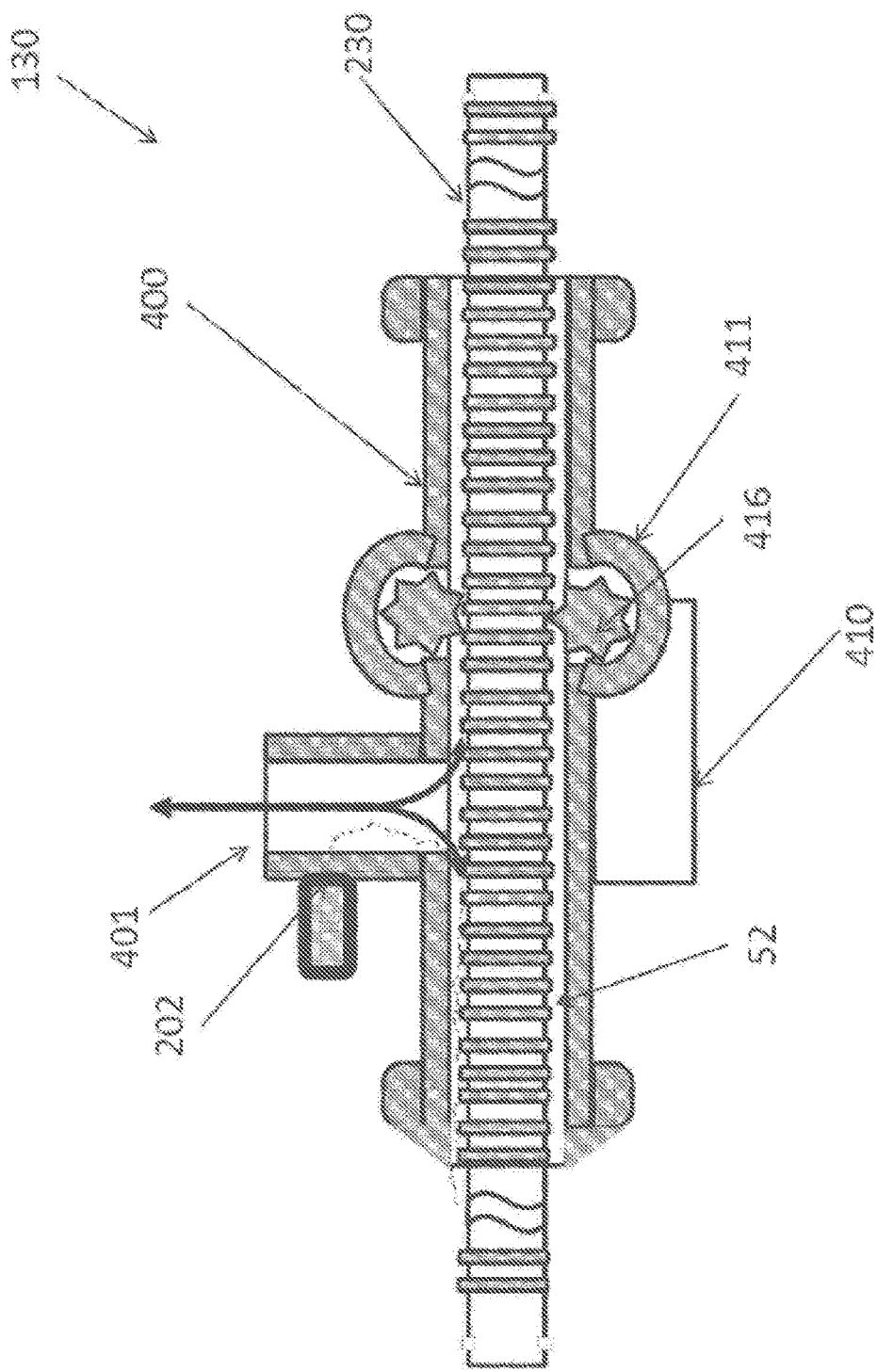
FIG. 13 is a schematic, cross-sectional illustration of an embodiment of a single-valve endoscopic probe, constructed and operative in accordance with the invention, featuring an grooved sheath and an advancing gear.
Figure 14:
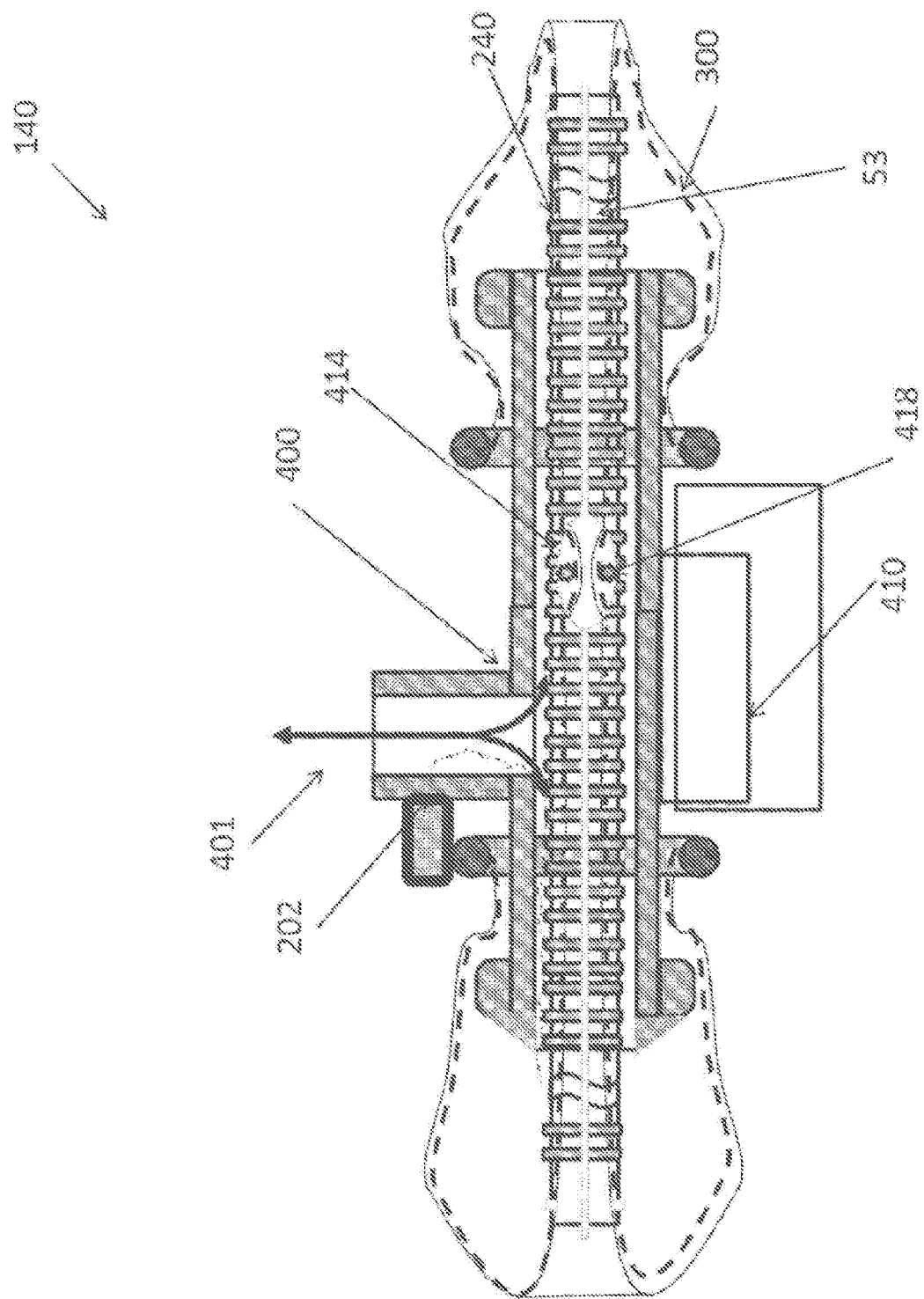
FIG. 14 is a schematic illustration of an embodiment of a single-valve endoscopic probe with flexible sleeve, constructed and operative in accordance with the invention, featuring a planetary advancing gear configured for operation in conjunction with the sleeve of FIG. 12 and/or with an optional internally serrated/indented sheath.

A sprocket wheel or another toothed or friction based mechanism (Examples are illustrated in FIGS. 13-14) can engage sheath 230 (or 220), and thereby force movement of sheath 230, back and forth, to effect insertion or retraction of sheath 230 into or out of colon 101, respectively. It is noted that sprockets 416 engage the external face of sheath 230 within bore 52 of valve unit 401 (or valve unit 40) where sheath 230 is not covered by sleeve 30.

Figure 12:
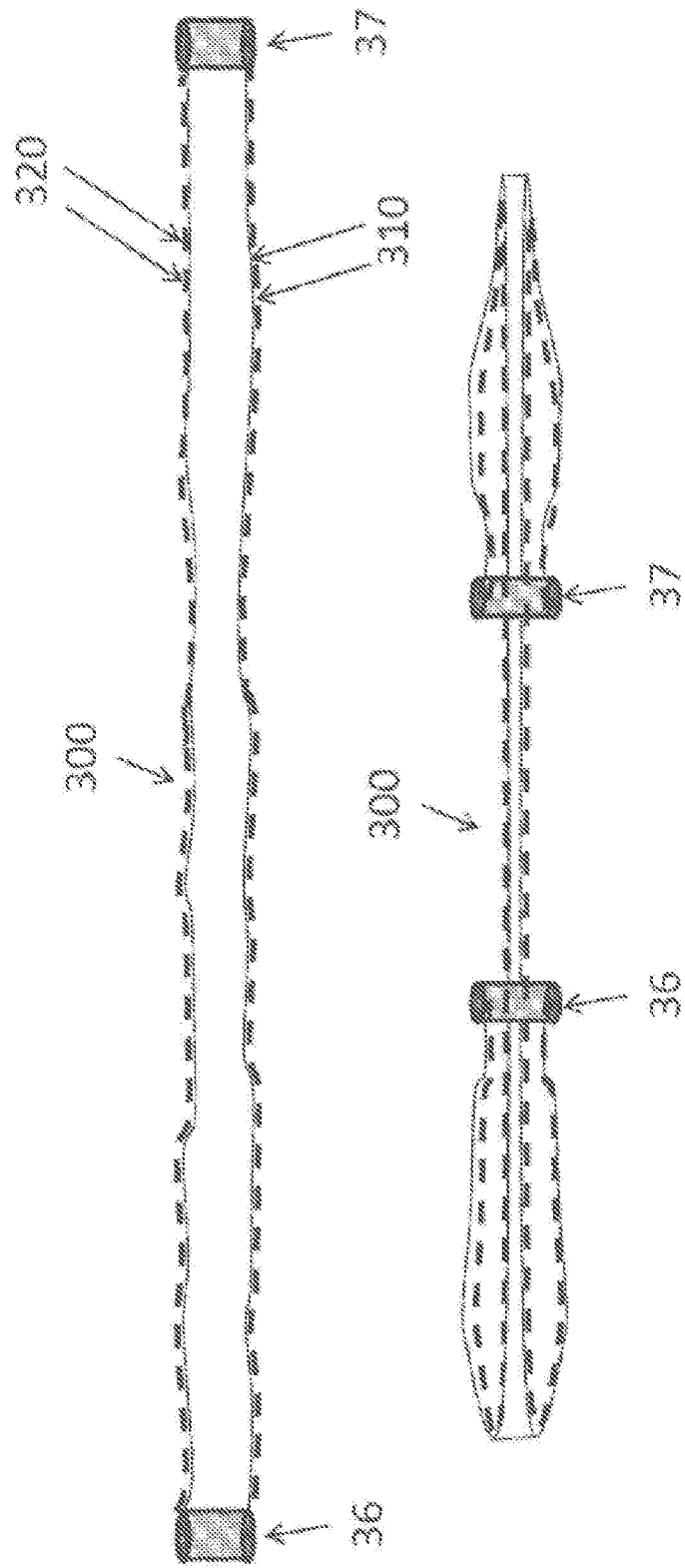
FIG. 12 includes schematic illustrations of an embodiment of an indented sleeve in extended and folded modes, constructed and operative in accordance with the invention, featuring indentations for facilitating advancing and centering of the sleeve.

An alternative configuration is shown in FIG. 12, which includes schematic illustrations of indented sleeve 300 in extended and folded modes, constructed and operative in accordance with the invention, featuring indentations 310 for facilitating advancing and centering of the sleeve. Indentations 310 can be external or internal circumferential notched recesses, grooves or depressions, separated by bulging protrusions 320, rendering the surface of indented sleeve 300 serrated or jagged, configured to engage a sprocket or a toothed propulsion mechanism that would force a pull of sleeve 300 toward the distal or proximal direction. Sheath 20 which is trapped within sleeve 300 would then be forced to advance or retreat, as sleeve 300 is forced to move toward the distal or proximal direction, respectively.

Further alternative configurations are shown in FIGS. 13-14. FIG. 13 is a schematic, cross-sectional illustration of an embodiment of single-valve endoscopic probe 130, constructed and operative in accordance with the invention, featuring an externally grooved sheath 230 and an advancing gear 413 (sleeve is not shown). The teeth of spur or sprocket 416 of planetary advancing gear 413 engage the externally grooved (or serrated, indented) surface of sheath 230, and thereby force movement of sheath 230, back or forth, to effect insertion or retraction of sheath 230 distal end wise or proximal end wise, respectively.

FIG. 14 is a schematic illustration of an embodiment of a single-valve endoscopic probe 140 with an optional flexible sleeve 300, an optional internally serrated/indented sheath 240, constructed and operative in accordance with the invention, featuring an advancing gear 414 configured for operation in conjunction with indented sleeve 300 of FIG. 12 and/or optional internally serrated/indented sheath 240. Spurs or sprocket wheels 418 are disposed within bore 53 of sheath 240. When sheath 240 is used, the teeth of sprocket 418 of advancing gear 414 engage the internally serrated/indented surface of sheath 240, and thereby force movement of sheath 240, back or forth, to effect insertion or retraction of sheath 230 distal end wise or proximal end wise, respectively. In addition or alternatively, sprocket 418 of advancing gear 414 is disposed between the internal face of sheath 240 (or sheath 20) the teeth of sprockets 418 engage the rugged surface of sleeve 300 that force a pull of sleeve 300 toward the distal or proximal direction. If sheath 20 is used, it is trapped within sleeve 300 and would then be forced to advance or retreat, as sleeve 300 is forced to move toward the distal or proximal direction, respectively. If sheath 240 is used the teeth of sprocket 418 of planetary advancing gear 414 engage the externally grooved surface of sheath 240 (in which case sleeve 30 is used or sleeve 300 is moved by a separate gear). An elongated central slit in sheath 240 (or sheath 20) provides for connecting wiring, or for a drive axle required to propel sprockets 418. Alternatively, advancing gear 414, which is isolated without wiring or mechanical connection to a propulsion conveying mechanism, can include electric motors mounted to sheath 20 that are induced to revolve by external electromagnetic fields, and pull sheath 240. Further optionally, the sleeve driving mechanism may be located outside sheath 240, inside valve unit 400, while engaging sleeve 300 through partially slotted sheath 240 or series of holes perforated along sheath 240 (similar to holes 210 of sheath 220 of FIG. 11) and matching the teeth steps of sprockets 418 and also accommodating the different translational movements of sheath 240 and sleeve 300.

Figure 15:
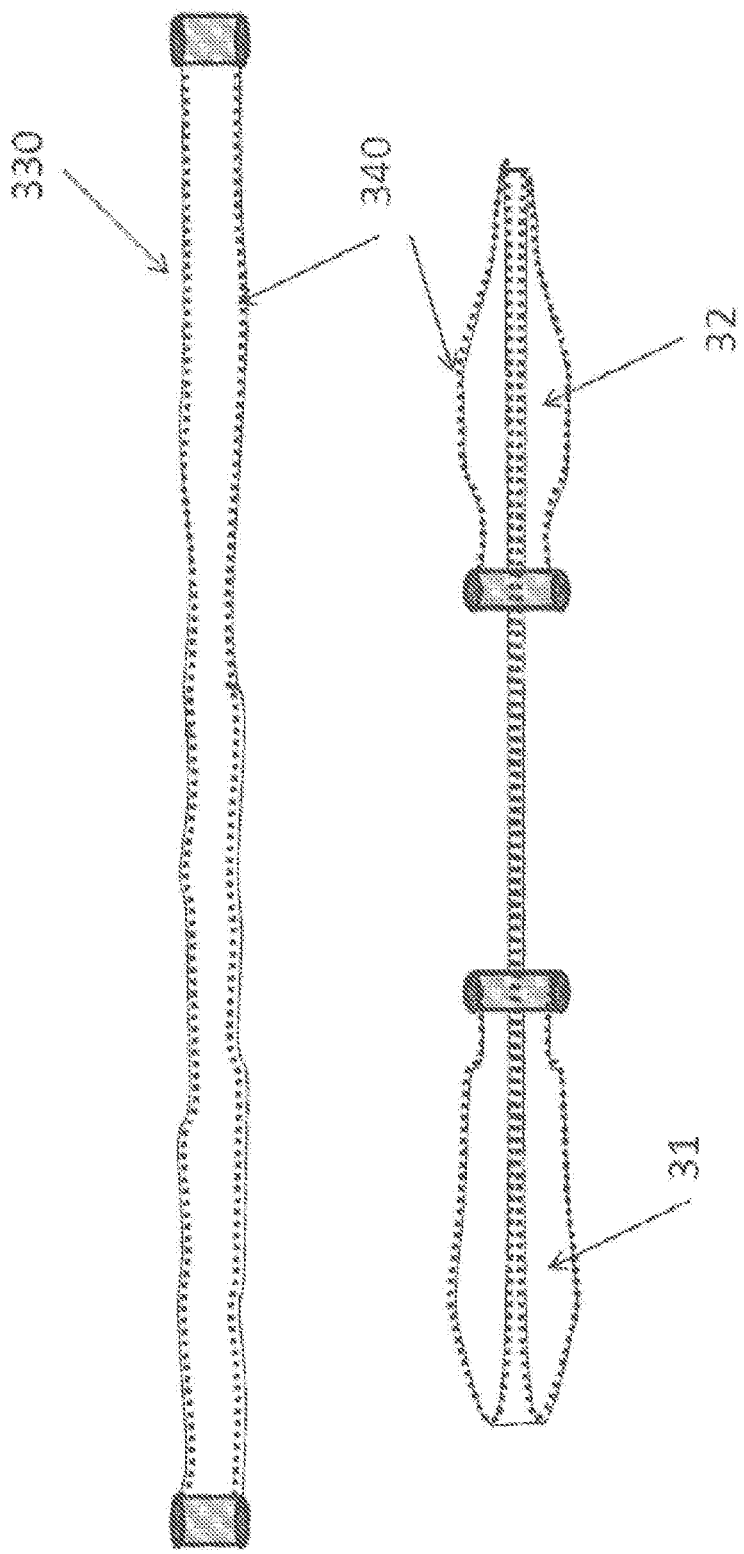
FIG. 15 is a schematic illustration of an embodiment of a sleeve in extended and folded modes, constructed and operative in accordance with the invention, featuring anesthetic/medical coating.

FIG. 15 is a schematic illustration of an embodiment of sleeve 330 in extended and folded modes, constructed and operative in accordance with the invention, featuring anesthetic deposit or coating, denoted 340. Anesthetic coating 340 overlays the internal face of sleeve 330. ('internal' when sleeve 300 is in an unfolded configuration as in the upper configuration of FIG. 15). When the proximal and distal portions 32 and 31 of sleeve 330 are folded inside out as shown in the bottom illustration of FIG. 15, to engage the configuration of covering sheath 20 and anchoring to valve unit 40, anesthetic coating 240 faces the external portion of probe 10 and thus is placed in direct contact with the internal wall of human colon 101, allowing release of anesthetic substances to the colon organs. The term 'anesthetic' or 'anesthetic/medical' refers to any and all medical substances, for effecting any medical treatment, soothing, lubricating or any other effect. Accordingly, despite its title, 'anesthetic' coating 340 is not limited to the inclusion of anesthetics, and may exclude anesthetics and/or other ingredients, such as markers that react to blood or any human body substance and may be used for indicating bleeding or bleeding location.

Figure 16:
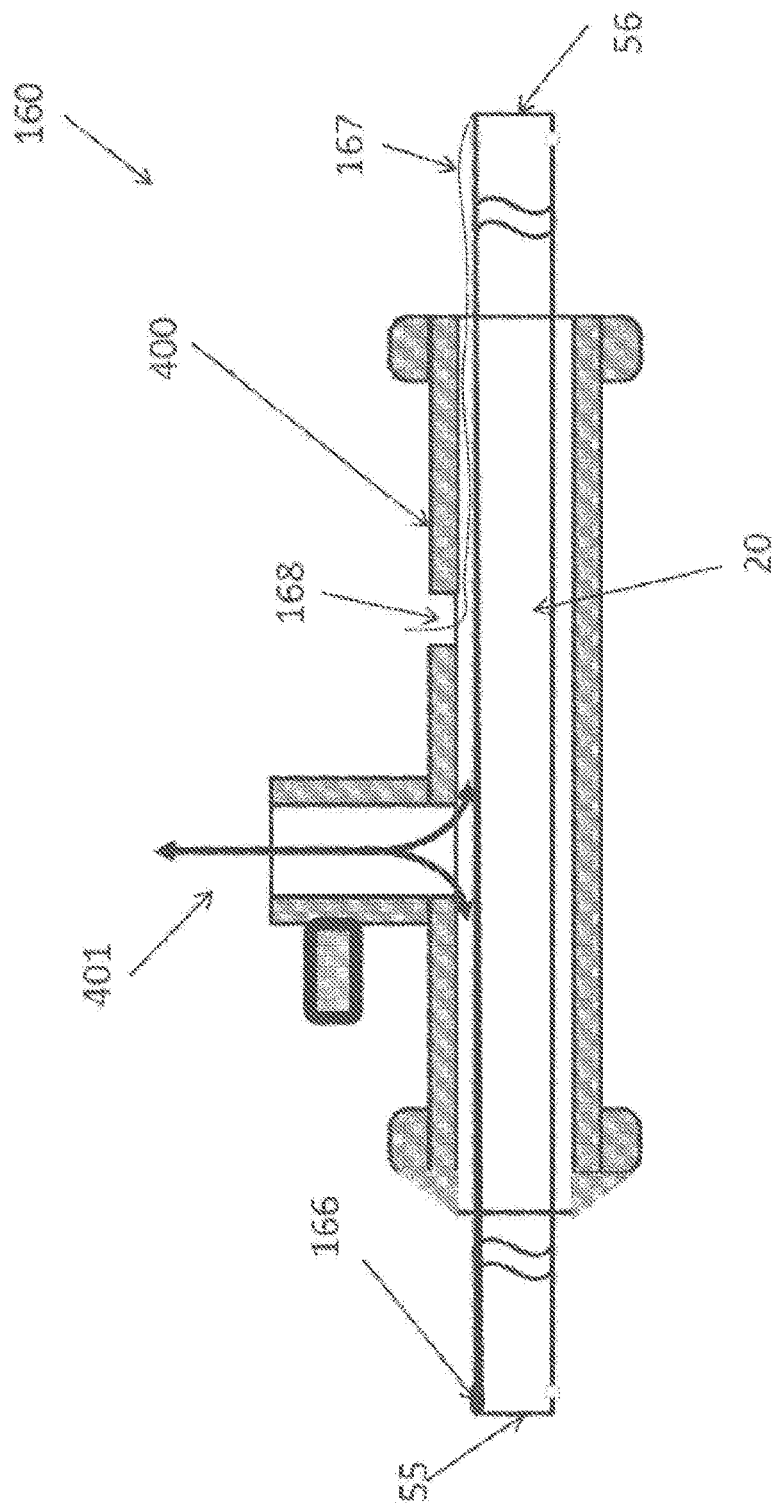
FIG. 16 is a schematic, cross-sectional illustration of an embodiment of a single-valve endoscopic probe, constructed and operative in accordance with the invention, featuring sheath-embedded camera.

FIG. 16 is a schematic, cross-sectional illustration of an embodiment of a single-valve endoscopic probe 160, constructed and operative in accordance with the invention, featuring sheath-embedded camera 166 (sleeve is not shown). Data and illumination wiring 167 is inserted through (hermetically sealed) aperture 168 valve unit 400 (or 40) and is further embedded along the entire length of the wall of sheath 20 from its proximal tip 56 to its distal tip 55. A camera 166 can include any known sensors as well as illumination, such as LED illumination, as well as treatment appliances which are not required to pierce sleeve 30.

Figure 17:
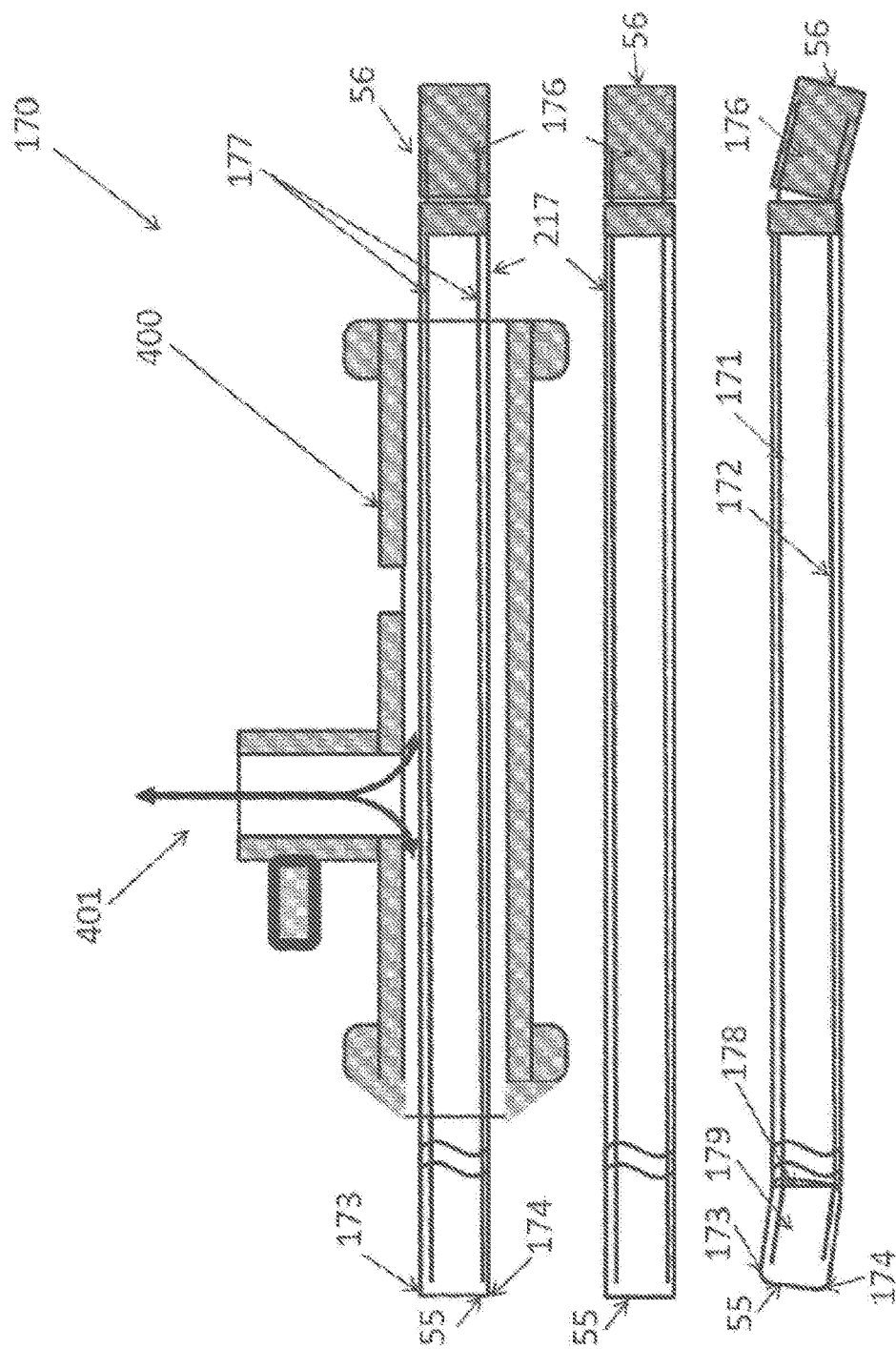
FIG. 17 includes schematic, cross-sectional illustrations of an embodiment of a single-valve endoscopic probe, constructed and operative in accordance with the invention, featuring sheath pulling wires for sheath tip angulation and steering.

FIG. 17 includes schematic, cross-sectional illustrations of an embodiment of a single-valve endoscopic probe 170, constructed and operative in accordance with the invention, featuring sheath pulling wires 177 for sheath tip angulation and steering (sleeve is not shown). A pair of oppositely disposed wires 177 is shown for demonstrating tip tilt angulation in a vertical axis. Alas, the rotation of sheath 217 for tip tilts in other axis may experience resistance when sheath 217 is warped with the windings of colon 101 and/or as the sleeve is inflated, accordingly further such pairs may be disposed along the internal circumference of sheath 20. Wires 177 are fixated to two opposed locations at distal tip 55. Wire 171 is connected at one end 173 of tip 55 and wire 172 is connected to the opposed end 174 of tip 55. A rigid portion 176 of sheath 217 is disposed at the proximal end 56 of sheath 217, and is separated therefrom, thereby allowing its tilting by the operator toward any of wires 171 or 172. When portion 176 is tilted toward wire 172, wire 171 is pulled and in its turn pulls tip 55 at its end 173. Sheath 217 is allowed to bend near its tip, such as by flexible or weakened section 178 or a hinged connection at section 178, and therefore tip portion 179 tilts toward tip end 173 and angulates sheath 217, to meet the winding required to adapt the curls of colon 101.

Figure 18:
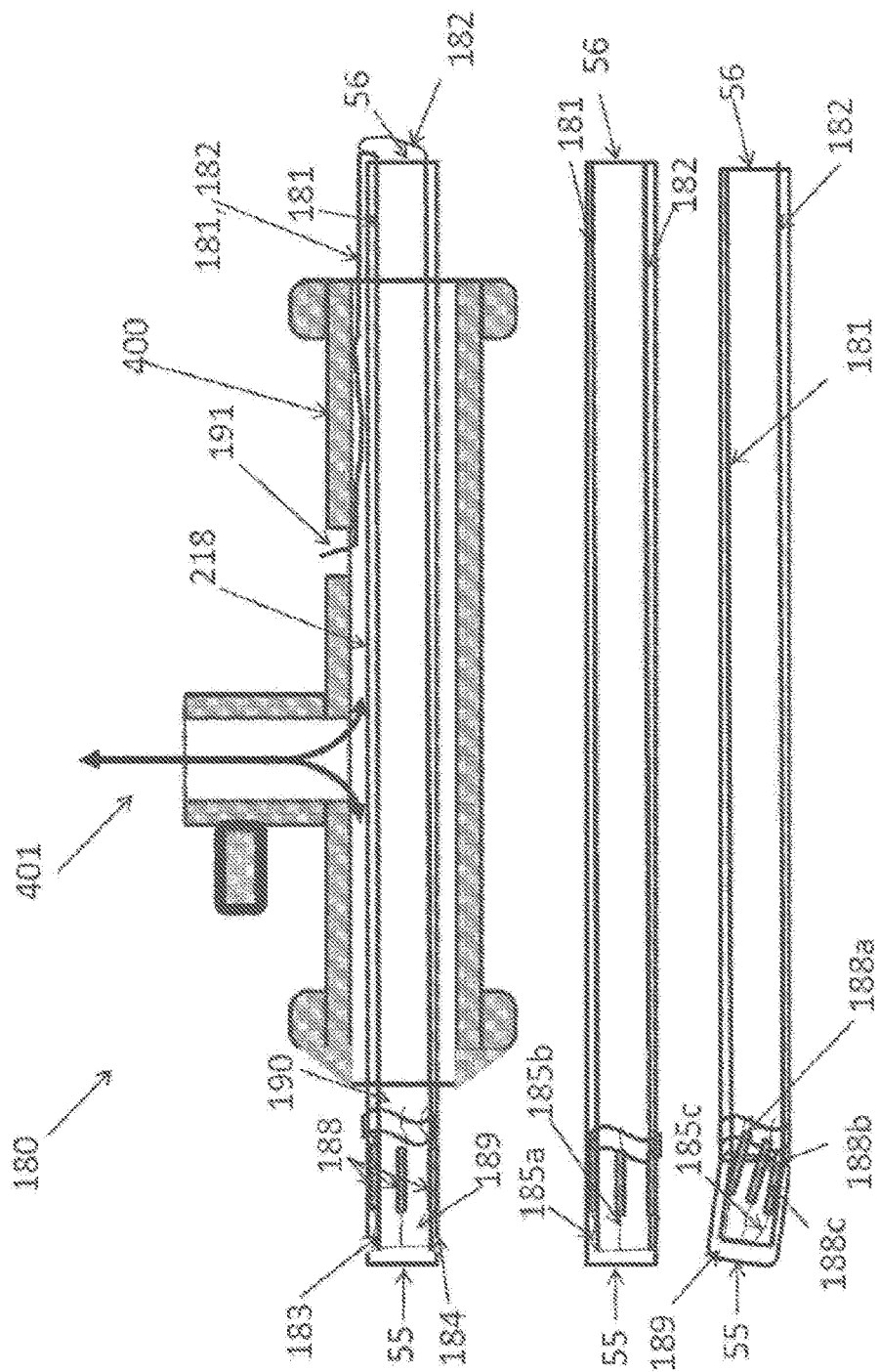
FIG. 18 includes schematic, cross-sectional illustrations of an embodiment of a single-valve endoscopic probe, constructed and operative in accordance with the invention, featuring sheath pulling wires with inchworm motors for sheath tip angulation and steering.

FIG. 18 includes schematic, sectional illustrations of an embodiment of a single-valve endoscopic probe 180, constructed and operative in accordance with the invention, featuring sheath pulling wires with inchworm motors 188 for sheath tip angulation and steering. Probe 180, includes sheath 218 and wires 181 and 182 which feed power and control to inchworm motors 188 and are disposed within sheath 218, and are curling about sheath proximal end 56 and (hermetically sealed) aperture 191 disposed in valve unit 400. Other types of motors or actuators may be applied instead of inchworm motors 188.

Wires 185a, 185b, 185c are disposed at distal tip 55, about tiltable tip portion 189, similar to the embodiment of FIG. 17. Inchworm motors 188a, 188b, and 188c, which are fixated to the sheath tip portion 190, grip wires 185a, 185b, 185c, respectively. Electrical supply (and control) wiring can extend along with wires 181, 182 or embedded within and along the wall of sheath 218. Activation of inchworm motor 188a pulls wire 185a and forces tip portion 189 to tilt upwards, toward motor 188a. Activation of both inchworm motors 188c and 188b pulls wires 185b and 185c and forces tip portion 189 to tilt toward motors 188c and 188b.

Figure 19:
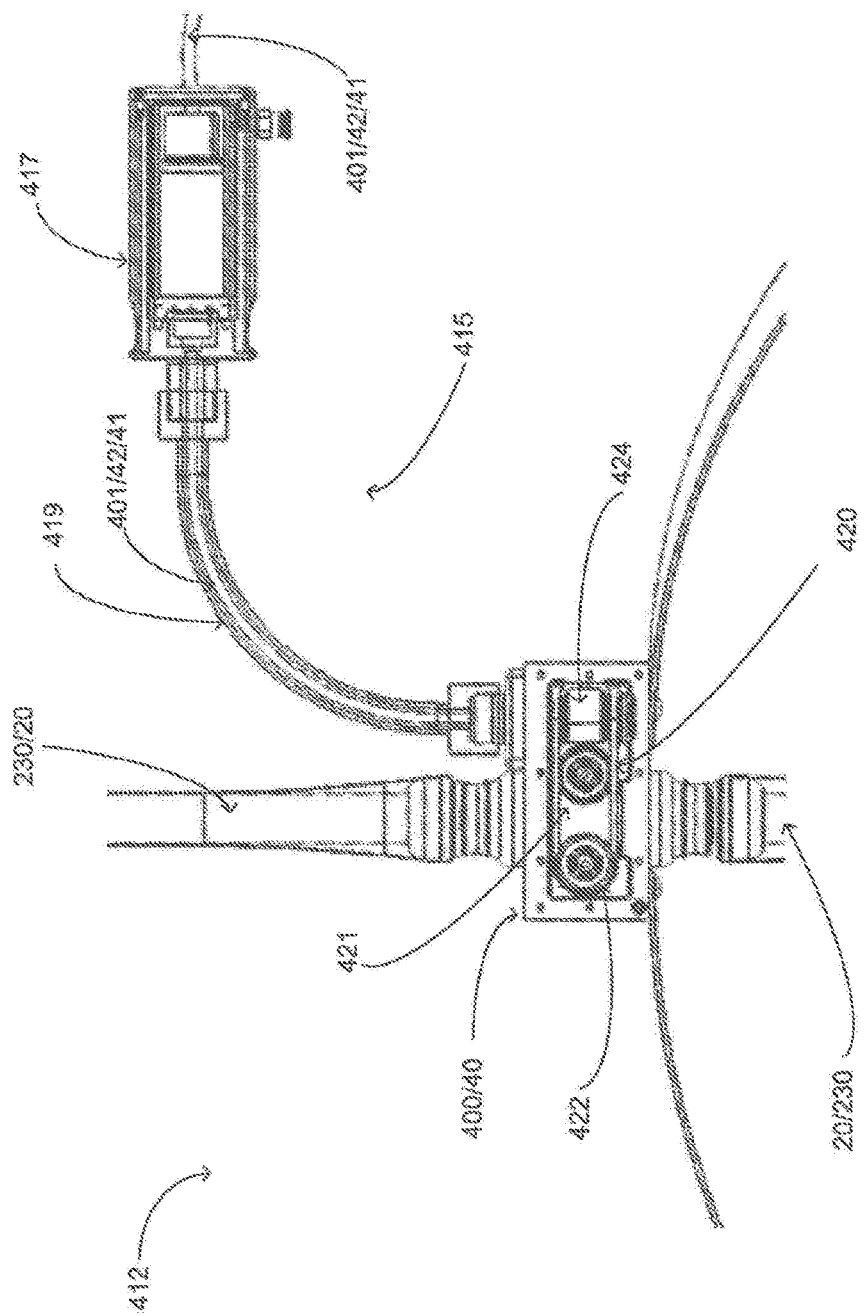
FIG. 19 is a schematic, cross-sectional illustration of an embodiment of a valve unit incorporating a drive mechanism for propelling an endoscopic probe, constructed and operative in accordance with the invention.
Figure 20:
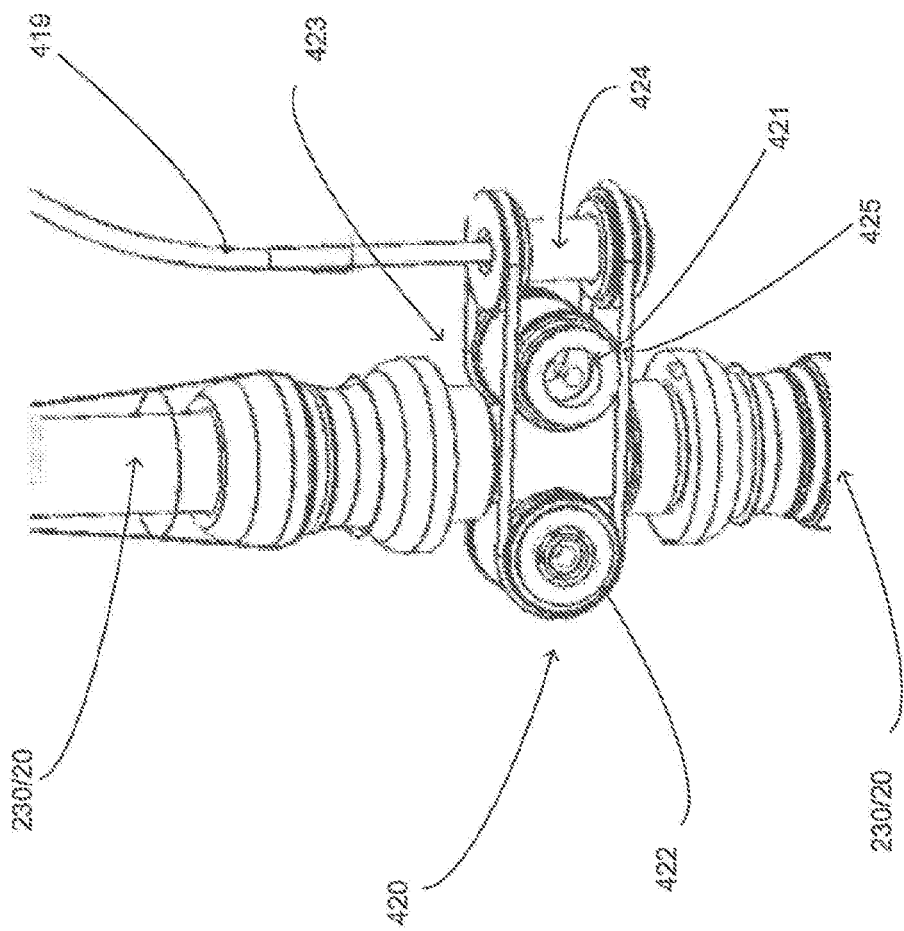
FIG. 20 is a schematic illustration of the torque splitter of the drive mechanism of FIG. 19.
Figure 21:
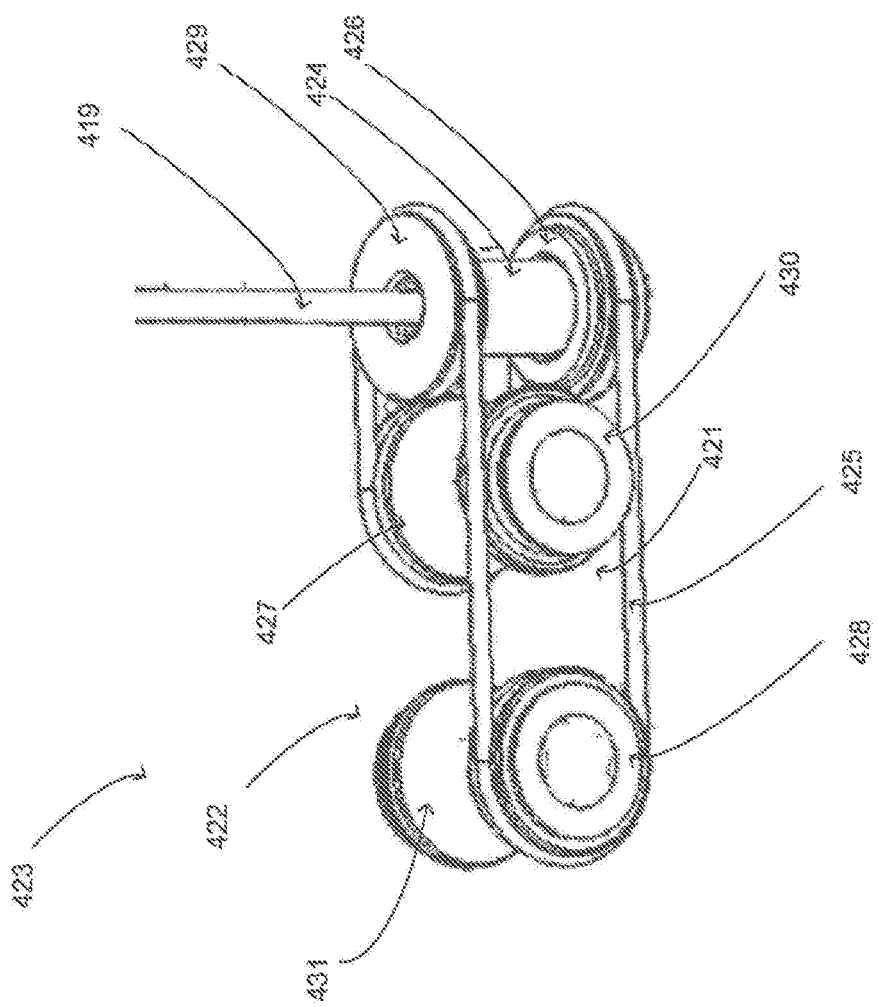
FIG. 21 is an enlargement of the compound pulley system of the torque splitter of FIG. 20.

FIG. 19 is a schematic, cross-sectional illustration of an embodiment of a valve unit 412 incorporating drive mechanism 415 for propelling an endoscopic probe, constructed and operative in accordance with the invention. Drive mechanism 415 is an example of a propulsion mechanism that can be applied for advancing gear 413 of FIG. 13, or adapted to advancing gear 414 of FIG. 14. Drive mechanism 415 is combined with components of valve unit 40 or 400. Drive mechanism 415 includes electrical motor unit 417, flexible drive shaft spindle 419, and torque splitter 420. Reference is now also made to FIGS. 20 and 21. FIG. 20 is a schematic illustration of torque splitter 420 of drive mechanism 415 of FIG. 19. FIG. 21 is an enlargement of compound pulley system 423 of torque splitter 420 of FIG. 20. Drive mechanism 415 further includes two output drive drums 421 and 422 that can operate, similar to sprockets 416 of FIG. 13, to advance or retract sheath 20 (or sheath 230) which is held between drums 421 and 422. A valve pipe designated 401/42/41, such as of valve 41, 42 or 401, enters valve unit 40 or 401 through flexible drive shaft spindle 419, and motor unit 417, wherein both—flexible drive shaft spindle 419, and motor unit 417 incorporate a passage therein to accommodate pipe 401/42/41 into valve unit 40 or 400. Flexible drive shaft spindle 419 can be formed as hollow shaft internally accommodating pipe 401/42/41. Alternatively, pipe 401/42/41 includes in internal pipe accommodating flexible drive shaft spindle 419. Electrical motor unit 417 turns flexible drive shaft spindle 419, which turns the two output drive shafts 421 and 422, via torque splitter 420, which is mounted inside valve unit 40 or 400, and embrace sheath 20 or 230 for its propulsion. Drive drums 424 and 426 are set up to furnish revolutions in two opposed rotational directions. Sheath 20 or 230 is held between drums 421 and 422 which roll along the longitudinal external sides of sheath 20 or 230 and thereby transfer their rotational movement into a linear movement of sheath 20 or 230, resembling sprocket wheels 416 of FIG. 13. Torque splitter 417 can incorporate any splitting mechanism, including differential, planetary, having spur gear trains, and the like. An example of one such splitting mechanism is compound pulley system 423. Torque splitter 417 includes input drum 424, two output drums 421 and 422, and endless taut cable or belt 425. Input drum 424 is connected to, and thereby rotated by, flexible drive shaft spindle 419, which conveys the rotational torque of electrical motor unit 417 to input drum 424. Input drum 424 is coupled with output drums 421 and 422 via endless belt 425, which serpentines to convey the torque from input drum 424 to output drums 421 and 422. Input drum 424 incorporates grooved input pulley 426. Output drum 421 features grooved output pulley 427 and output drum 422 features grooved output pulley 428. A freely rotatable sheave pulley 429 is also disposed about drum 424 or coupled therewith, such as by ball bearing that isolates sheave pulley 429 from the rotations of drum 424. Endless belt 425 is wound about an arc of contact of each of pulleys 426, 427, 428, and 429 in circumferential grooves laterally disposed in the rim of pulleys 426, 427, 428 and 429, providing the adequate friction with belt 425, such that the driving force applied by pulley 426, drives belt 425, and belt 428 drives pulleys 427 and 428. If required, toothed interface is provided to belt 425, and pulleys 426, 427, and 428 to increase the bilateral grip between belt 425 and each of pulleys 426, 427, and 428. However, sheave pulley 429 is provided only as a looped around pulley without transfer of force. Endless belt 425 is looped around pulleys 427 and 428, which are disposed toward opposite directions and runs along two parallel paths between pulleys 427 and 428, both paths curling about pulleys 426, 429, thereby, belt 425 rotates pulleys 427 and 428 in the opposite rotational direction. Pulleys 427 and 428 are connected to drums 421 and 422, respectively. Each of drums 421,422, may now be coupled with sheath 20 or 230, directly or through any adequate engaging or coupling arrangement, such as wheels 430, 431, which are connected to drums 421, 422, respectively, and which can be sprocket wheels, similar to sprockets 416 or 418.

Figure 22:
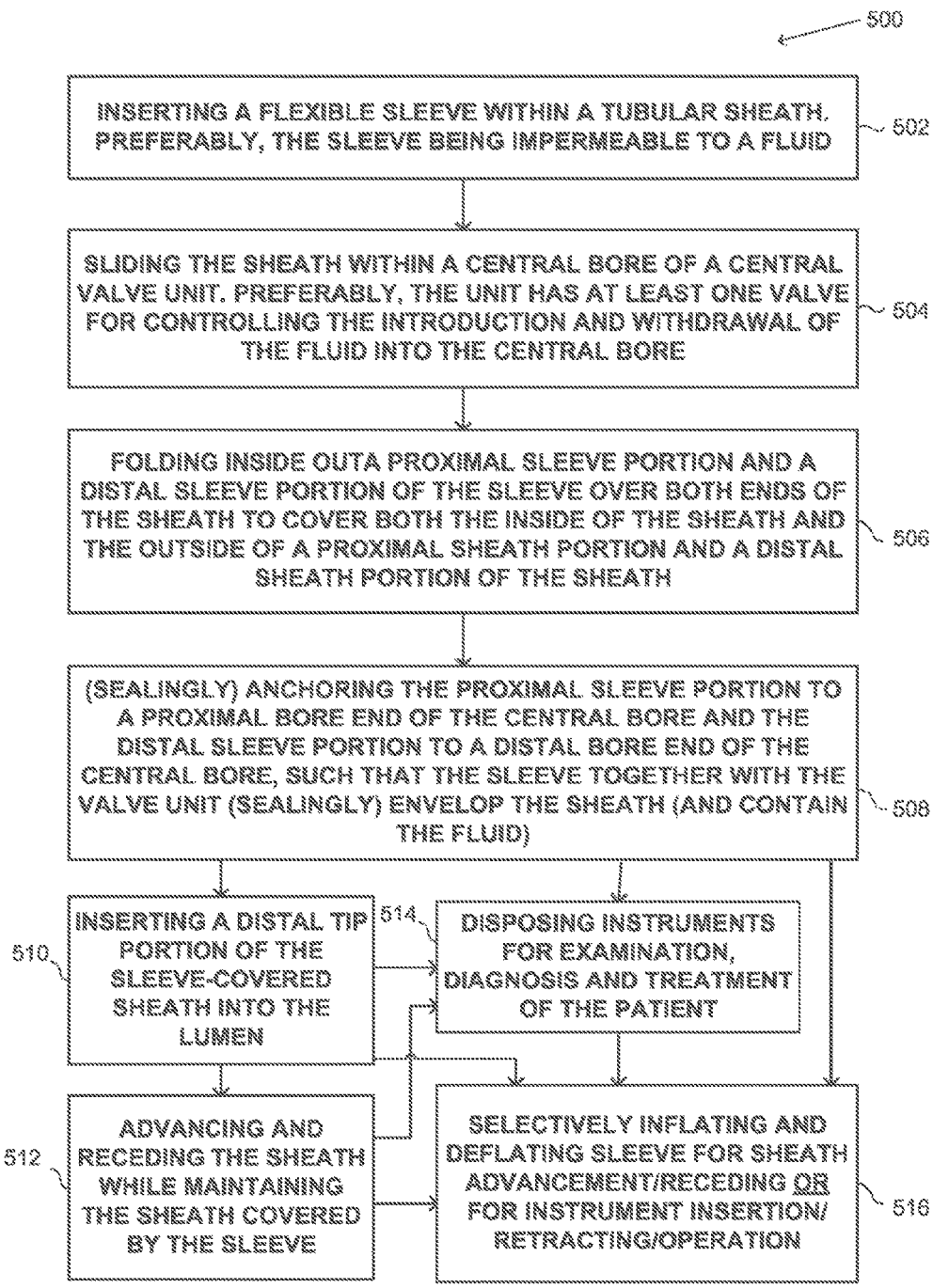
FIG. 22 is a block diagram of a method for propelling an endoscopic probe within a lumen, operative in accordance with an embodiment of the disclosed invention.

Reference is now made to FIG. 22, which is a block diagram of a method 500 for propelling an endoscopic probe within a lumen, operative in accordance with an embodiment of the disclosed invention.

In procedure 502, a flexible sleeve is inserted within a tubular sheath. With reference to FIGS. 1-5, sleeve 30 is inserted within sheath 30. Preferably, the sleeve is impermeable to a fluid. The fluid may be gas, pressurized gas, or liquid. Optionally, a portion of the sleeve includes a variable diameter to accommodate variable lumen, such as sleeve 35 of FIG. 6. Further optionally, a face of the sleeve is coated/deposited with an anesthetic or other medical substance, such as sleeve 330 of FIG. 15.

In procedure 504, the sheath is slid through a central bore of a central valve unit, such as sheath 20 which is slid through bore 52 in FIGS. 1-5. Preferably, the central valve unit includes at least one valve for controlling the introduction and withdrawal of the fluid into the central bore. In reference to FIGS. 1-5 and 7, central valve unit 40 includes two valves, 41, 42, while central valve unit 400 in FIGS. 10, 11, 13, 14, and 16-18, includes a single valve 401.

In procedure 506, a proximal sleeve portion, and a distal sleeve portion of said sleeve are folded inside out over both ends of the sheath to cover both the inside of the sheath and the outside of a proximal sheath portion and a distal sheath portion of the sheath. In reference to FIGS. 1-5, proximal sleeve portion 32, and distal sleeve portion 31 of sleeve 30 are folded inside out over both ends 55, 56 of sheath 20 to cover both the inside face internal bore 53 of sheath 20 and the outside of proximal sheath portion 22 and distal sheath portion 21 of sheath 20.

In procedure 508, the proximal sleeve portion is anchored to a proximal bore end of the central bore the distal sleeve portion is anchored to a distal bore end of the central bore, such that the sleeve together with the valve unit envelop the sheath. Preferably, the proximal sleeve portion is sealingly anchored to the proximal bore end of the central bore, and the distal sleeve portion is sealingly anchored to the distal bore end of the central bore, such that the sleeve together with the valve unit sealingly contain the fluid, while the sleeve is impermeable to the fluid (as mentioned in procedure 502) and while the central valve unit includes at least one valve for controlling the introduction and withdrawal of the fluid into the central bore (as mentioned in procedure 504). In reference to FIGS. 1-5, proximal sleeve portion 31 is sealingly anchored to proximal bore end of central bore 52 at anchoring 23, distal sleeve portion 32 is sealingly anchored to distal bore end 50 of central bore 52 at anchoring 23, such that sleeve 30 together with valve unit 40 envelop sheath 20.

In procedure 510, a distal tip portion of the sleeve-covered sheath is inserted into the lumen, similar to the configuration of probe 10 in FIG. 1, for initiating the insertion of distal portion 21 of sheath 20 into lumen 101, as shown in FIGS. 2-5.

In procedure 512, the sheath is advanced and retracted, as required to serve the medical procedure, while maintaining the sheath covered by the sleeve, as is shown in several configurations in FIGS. 1-5.

The above procedures provide for the effective operation of method 500 for propelling an endoscopic probe within a lumen. It is noted that the method is primarily intended to be applied with a fluid, namely such that the sleeve together with the valve unit sealingly contain the fluid (procedure 508). To that preferable end, the central valve unit includes at least one valve for controlling the introduction and withdrawal of a fluid into said central bore (procedure 504), the sleeve is impermeable to the fluid (procedure 502), and the anchoring comprises sealingly anchoring the proximal sleeve portion to a proximal bore end of the central bore and the distal sleeve portion to a distal bore end of the central bore, such that the sleeve together with the valve unit sealingly envelop the sheath (procedure 508).

In procedure 514, instruments for examination, diagnosis and treatment of the patient are disposed in at least one of: within the central bore of the sheath outside the sleeve, within the central bore of the sheath within the sleeve, when inserted between the sheath and the sleeve, embedded in the sheath, deployed beside the sheath within the sleeve, and deployed beside said sheath outside said sleeve. In reference to FIG. 5, the wiring of instrument 80 is disposed within central bore 53 of sheath 20 outside sleeve 30. In FIG. 9, instrument 80 is combined in rod 47 which is disposed within central bore 53 of sheath 20 outside sleeve 30. In FIGS. 7, 10, 11, 13, 14, forward illumination 202, including wiring, is inserted between sheath 20 and bore 52 within the sleeve for facilitating inspection around distal edge 55 of distal portion 21 of sheath 20 when inserted within colon 101 of human body 100, and camera 166 is embedded in sheath 30 as exemplified in FIG. 16. Procedure 514 is performed before procedure 502 or in parallel to any of procedures 504-508, corresponding the desired location of the instrument with regard to the central bore, the sheath and the sleeve.

In procedure 516, the sleeve, or a portion thereof, is selectively inflated or deflated for sheath advancement/receding or for instrument insertion/retracting/operation. Procedure 516 may be performed after procedures 508, 510, 512, or 514, or in lieu of, or simultaneously with, procedures 510, 512, or 514. As noted above with reference to FIG. 5, deflation of sleeve 30 may involve complete extraction of fluid therefrom to the extent sleeve 30 is tightly adhered by the internal vacuum created within sleeve 30 to both sides of sheath 20, rendering both into an overtube-like configuration, leaving clear and wide passage within bore 53 for convenient insertions and retractions of diagnostic tools and instruments. When the sleeve is inflated and is advanced or retracted in conjunction with, or for the sake of, advancing or receding the sheath within colon 101, the portion of the sleeve disposed within the bore of the sheath advances/retracts twice the length the sheath advances/recedes, while typically grasping and carrying the inserted tool/instrument. Accordingly, the sleeve can be deflated, intermittently—if required, for allowing an offsetting reverse push or pull of the inserted object within bore 53, and thereby to compensate over-progression. The sheath may be perforated for easy passage of fluid within the sleeve, allowing fast inflating and deflating of the sleeve. In reference to FIG. 11, sheath 220, allows easy passage of fluid, liquid or gas, and for fast inflating and deflating of the sleeve.

Figure 23:
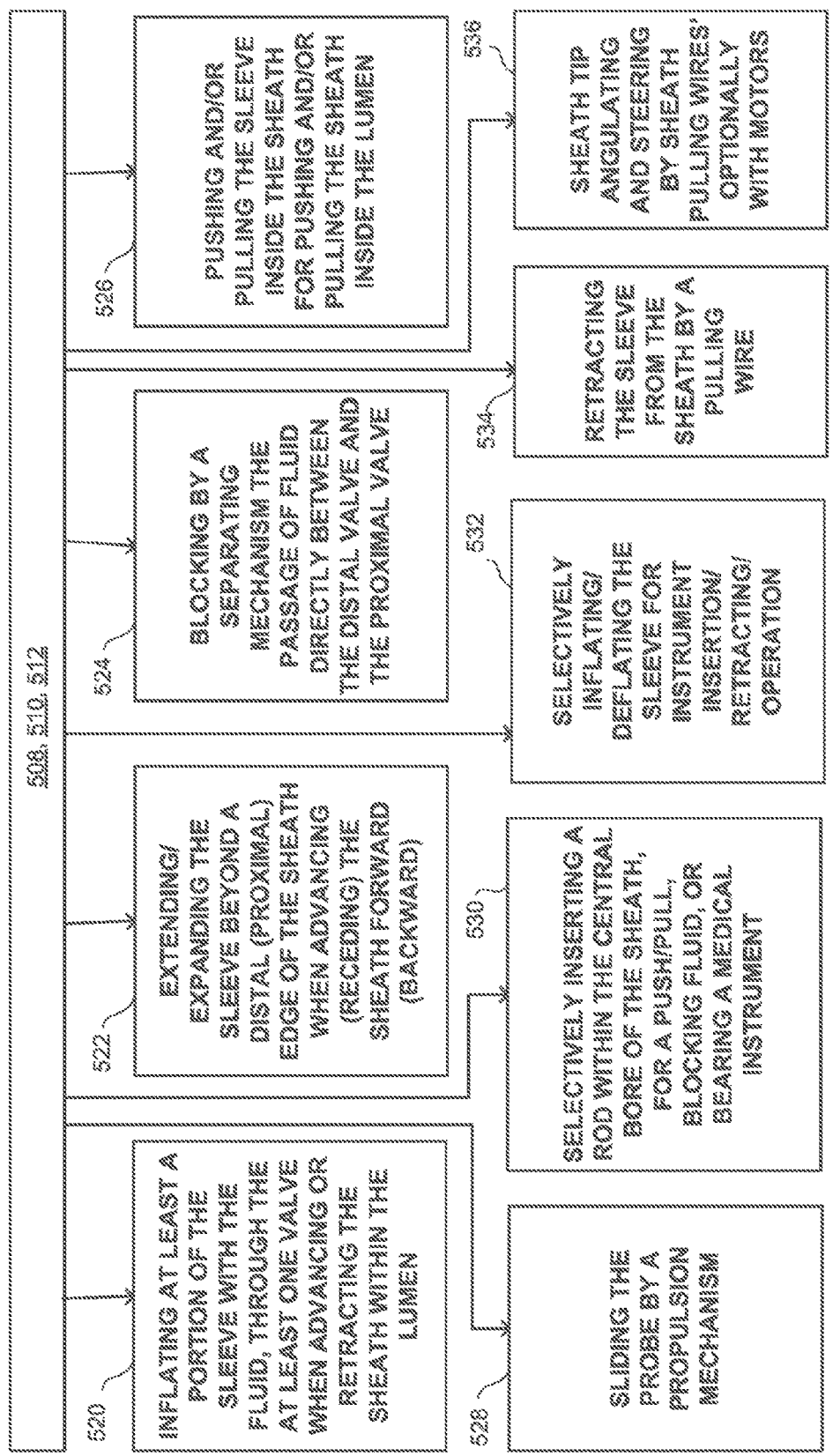
FIG. 23 is a block diagram of sub-procedures of procedure 520 of the embodiment of FIG. 22.

Method 500 may include further optional or preferable procedures and features outline below. Reference is now made to FIG. 23 which is a block diagram of sub-routines or sub-procedures of procedure 516 of the embodiment of FIG. 22. Accordingly, procedure 516 may further include any of sub-procedures 520-536.

In sub-procedure 520, at least a portion of the sleeve is inflated with the fluid, through the at least one valve, when advancing or retracting the sheath within the lumen. Preferably, a distal side of the sleeve is inflated to insert the probe (while the proximal side of the sleeve may be allowed to deflate, or actively deflated), and a proximal side of the sleeve is inflated to extract the probe (while the distal side of the sleeve may be allowed to deflate, or actively deflated), using the central valve unit. In reference to FIGS. 1-5, distal side 31 or pocket 33 of sleeve 30 is inflated to insert probe 10 (while proximal side 32 or pocket 34 of sleeve 30 may be allowed to deflate, or is actively deflated), and proximal side 32 of sleeve 30 is inflated to extract probe 10 (while distal side 31 or pocket 33 of sleeve 30 may be allowed to deflate, or is actively deflated), using central valve unit 40.

In sub-procedure 522, the sleeve is extended/expanded beyond a distal edge of the sheath when advancing the sheath forwards, or beyond a proximal edge of the sheath when receding the sheath backwards. Preferably, the at least one valve mentioned in procedure 504 includes a distal valve and a proximal valve. The sleeve is extended/expanded beyond a distal edge of the sheath, as fluid is introducing into a distal portion of the sheath through the distal valve and the sheath advances forward. The sleeve is extended/expanded beyond a proximal edge of the sheath, as fluid is introduced into a proximal portion of the sheath through the proximal valve and the sheath advances backward. In reference to FIGS. 1-5, sleeve 30 is extended/expanded beyond distal edge 55 of sheath 20, as fluid is introducing into distal portion 21 of sheath 20 through distal valve 41 and sheath 20 advances forward. Sleeve 30 is extended/expanded beyond proximal edge 56 of sheath 20, as fluid is introduced into proximal portion 22 of sheath through proximal valve 42 and sheath 20 advances backward.

In sub-procedure 524, the passage of fluid directly between the distal valve and the proximal valve is blocked by a separating mechanism. In reference to FIGS. 1-5 and 7, O-ring 43, as well as head 48 of rod 45 in FIG. 4, and optional separating mechanism 44 in FIG. 1, block passage of fluid directly and between distal valve 41 and proximal valve 42.

In sub-procedure 526, the sleeve is pushed and/or pulled inside the sheath for pushing and/or pulling the sheath inside the lumen. In reference to FIG. 4, head 48 of rod 45 pushes and/or pulls sleeve 30 inside sheath 20 for pushing and/or pulling sheath 20 inside lumen 101. In FIG. 14, mechanism 411 pushes and/or pulls sleeve 300 inside sheath 240 for pushing and/or pulling sheath 24 inside the lumen.

In sub-procedure 528, which may optionally be performed as a sub-procedure of procedure 504 and/or procedure 502, the probe is slid by a propulsion mechanism. The mechanism may include a sprocket wheel, a toothed mechanism, a friction based mechanism, an indented sleeve, a perforated sheath, a slotted sheath, an externally serrated/indented sheath, and/or an internally serrated/indented sheath. In reference to FIGS. 11-14, the probe is slid by propulsion mechanisms 411, 414, featuring sprocket wheels 416, 418 which are part of toothed mechanisms 411, 414, which are also examples of friction based mechanisms, indented sleeve 300 of FIG. 12, a perforated sheath as of FIG. 11, and slotted sheath or externally or internally serrated/indented sheath as of FIGS. 13 and 14.

In sub-procedure 530, which may optionally be performed as a sub-procedure of procedure 504 and/or procedure 502, a rod is selectively inserted within the central bore of the sheath, wherein the rod includes at least one of: a bulbous head for facilitating push/pull of the sheath, an expandable head for facilitating push/pull of the sheath, an expandable head for selectively blocking fluid flow inside the sleeve at a blocking location disposed within the bore of the sheath, and an instrument for examination, diagnosis and treatment of the patient. In reference to FIGS. 4 and 9, rod 45 is selectively inserted within central bore 53 of sheath 20, wherein the rod may incorporate a bulbous head 48 for facilitating push/pull of sheath 20, an expandable head 49 of rod 46 for facilitating push/pull of sheath 20 and/or for selectively blocking fluid flow inside sleeve 30 at a blocking location disposed within bore 53 of sheath 20, or instrument 80 for examination, diagnosis and treatment of the patient.

In sub-procedure 532 the sleeve is selectively Inflated and deflated for instrument insertion/retracting/operation. Deflation of the sleeve may involve complete extraction of fluid therefrom to the extent the sleeve is tightly adhered by the internal vacuum created within the sleeve to both sides of the sheath, rendering both into an overtube-like configuration (sleeve-"coated" sheath). Such a configuration leaves the widest possible clear passage within the bore of the sheath for convenient insertions and retractions of diagnostic tools and instruments, such as used, for instance, in polyp removal surgery.

As is noted with reference procedure 516 and elaborated with reference to FIG. 5, when sleeve 30 is inflated and is advanced or retracted in conjunction with, or for the sake of, advancing or receding the sheath within colon 101, according to procedure 520 or procedure 522, the portion of the sleeve disposed within the bore of the sheath advances/retracts twice the length sheath advances/recedes, and is typically clenched inwardly about the central axis of the bore. As a result, any object inserted through the sleeve, such as tool 80 in FIG. 5 (particularly its cable or rod) or rod 45 in FIG. 4, is firmly grasped by the inflated, inwardly clenching, sleeve which typically grasps and carries the inserted object twice the length by which the sheath progresses (to either direction). Accordingly, to avoid over-progression of the inserted object, the sleeve can be deflated, intermittently—if required, for allowing an offsetting reverse push or pull of the inserted object within the bore of the sheath, compensating for its already-occurred or prospective over-progression.

In sub-procedure 534, the sleeve is retracted from the sheath by a pulling wire, such as wire 38 in FIG. 8. This may also serve for the entire removal of the disposable sleeve, after the medical procedure is completed, allowing the insertion of a new sleeve for the next medical procedure.

In sub-procedure 536, the sheath tip is angulated and/or steered by sheath pulling wires. Optionally, the wires may be pulled by motors, such as inchworm motors. With reference to FIG. 17, sheath tip 179 is angulated and/or steered by sheath pulling wires 177, 171, 172. In reference to FIG. 18, wires 185*a*, 185*b*, 185*c*, may be pulled by motors 188, such as inchworm motors 188*a*, 188*b*, 188*c*.

Although preferred embodiments are described hereinabove with reference to a device for moving an instrument through the lower gastrointestinal tract, it will be understood that the novel principles of the present invention may be used to move objects in other body cavities, such as, the throat or lungs, and may also be used to move objects in lumens and other regions for non-medical applications, as well. It is also understood that while the preferred embodiments described hereinabove have physical data leads and control leads, the propulsion and instrument package can be powered by batteries and can store data and/or transmit data by wireless communications, as is known in the art.

It will thus be appreciated that the preferred embodiments are cited herein by way of example, and the full scope of the invention is limited only by the claims.

While certain embodiments of the disclosed subject matter have been described, so as to enable one of skill in the art to practice the present invention, the preceding description is intended to be exemplary only. It should not be used to limit the scope of the disclosed subject matter, which should be determined by reference to the following claims.

The invention claimed is:

1. A hollow probe for advancing and retracting medical instruments within an internal lumen, the hollow probe comprising:
   a central valve unit external to a body of the patient and including a central bore and at least one valve, the at least one valve configured for controlling introduction and withdrawal of fluid into the central bore;
   a tubular sheath having an intermediate portion between a proximal portion and a distal portion, the tubular sheath insertable into and slidably movable within the central bore such that the central valve unit encircles the intermediate portion and the proximal and distal portions extend from the central bore; and
   a flexible sleeve impermeable to fluid having first and second ends; the flexible sleeve attached at the first end to a proximal end of the central valve unit and attached at the second end to a distal end of the central valve unit,
   wherein the flexible sleeve is folded over tips of the tubular sheath and inverted to cover both inside and outside surfaces of the proximal and distal sheath portions of the tubular sheath such that the flexible sleeve envelopes the tubular sheath containing fluid and allowing sliding of the tubular sheath within the central bore.

2. The probe according to claim 1, wherein the fluid introduced into or withdrawn from the central bore is a gas, a pressurized gas, or a liquid.

3. The probe of claim 1, wherein a distal side of said sleeve is inflated in order to propel said sheath forward within the lumen, and a proximal side of said sleeve is inflated in order to propel the probe backward within the lumen.

4. The probe of claim 1 wherein the hollow probe is configured such that the flexible sleeve extends or expands beyond a distal edge of the tubular sheath as the tubular sheath advances forward, and the flexible sleeve extends or expands beyond a proximal edge of the tubular sheath as the tubular sheath recedes backward.

5. The probe of claim 4, wherein said at least one central valve unit comprises a distal valve and a proximal valve, and wherein said sleeve extends/expands beyond a distal edge of said sheath, as fluid is introduced into a distal portion of said sheath through said distal valve and said sheath advances forward, and wherein said sleeve extends/expands beyond a proximal edge of said sheath, as fluid is introduced into a proximal portion of said sheath through said proximal valve and said sheath recedes backward.

6. The probe according to claim 5, further comprising a separating mechanism for blocking passage of fluid directly between said distal valve and said proximal valve.

7. The probe according to claim 1, wherein a pushing and/or pulling mechanism is used to push or pull said sleeve inside said sheath.

8. The probe according to claim 1, further comprising a propulsion mechanism for sliding the probe, wherein said mechanism comprises at least one selected from the list consisting of:
   sprocket wheel;
   toothed mechanism;
   friction based mechanism;
   indented sleeve
   grooved sheath
   slotted sheath;
   externally serrated/indented sheath; and
   internally serrated/indented sheath.

9. The probe according to claim 1, further comprising a rod which can be selectively inserted within the central bore of said sheath, said rod comprising at least one of:
   bulbous head for facilitating push/pull of said sheath;
   expandable head for facilitating push/pull of said sheath;
   expandable head for selectively blocking fluid flow inside said sleeve at a blocking location disposed within the bore of said sheath; and
   instrument for examination, diagnosis and treatment of the patient.

10. The probe according to claim 1, further comprising an instrument for examination, diagnosis and treatment of the patient the instrument:
   disposed within the central bore of the tubular sheath outside of the flexible sleeve;
   disposed within the central bore of the tubular sheath within the flexible sleeve, the instrument inserted between the tubular sheath and the flexible sleeve;
   embedded in the tubular sheath;
   deployed beside the tubular sheath within the flexible sleeve; or
   deployed beside the tubular sheath outside the flexible sleeve.

11. The probe according to claim 1, wherein said sheath comprises a perforated sheath allowing passage of fluid there through.

12. The probe according to claim 1, further comprising a sleeve pulling wire for assisting retraction of said sleeve from said sheath.

13. The probe according to claim 1, further comprising pulling wires for angulation of a tip of the tubular sheath and for steering of the tubular sheath.

14. The probe according to claim 13, further comprising motors for pulling said pulling wires.

15. The probe according to claim 1, wherein at least a portion of the flexible sleeve has a variable diameter for accommodating an internal lumen of variable diameter.

16. The probe according to claim 1, wherein said sleeve comprises anesthetic coating or deposit laid over a face of said sleeve.

17. The probe according to claim 1, further comprising an anus adaptor connected to the distal end of the central valve unit, the anus adaptor positioning the central valve unit adjacent an anus of the patient during operation.

18. The probe according to claim 17, wherein an opening of the anus adaptor is configured for engaging a tip of the distal end of the central valve unit.

19. A method for propelling a hollow probe within an internal lumen, the probe enabling insertion, advancement, and retraction of medical instruments within the internal lumen, the method comprising:
   inserting a flexible sleeve within a tubular sheath, the flexible sleeve impermeable to fluid and the tubular sheath having a proximal portion, an intermediate portion, and a distal portion;
   sliding the intermediate portion of the tubular sheath within a central bore of a central valve unit and extending the proximal and distal portions of the tubular sheath from the central bore, the central valve unit external to a body of a patient;
   folding a proximal portion of the flexible sleeve inside out over the proximal portion of the tubular sheath covering both an inside surface and an outside surface of the proximal portion of the tubular sheath;

folding a distal portion of the flexible sleeve inside out over the distal portion of the tubular sheath covering both an inside surface and an outside surface of the distal portion of the tubular sheath;

anchoring the proximal portion of the flexible sleeve to a proximal end of the central bore and anchoring the distal portion of the flexible sleeve to a distal end of the central bore, such that the flexible sleeve and the central valve unit envelop the tubular sheath, the anchoring forming a seal to contain fluid;

inserting a distal tip portion of a tip of the tubular sleeve into the internal lumen; and advancing and retracting the tubular sheath within the internal lumen, wherein the flexible sleeve and the central valve unit envelop the tubular sheath throughout operation of the hollow probe.

20. The method according to claim 19, further comprising controlling introduction and withdrawal of fluid into the central bore using at least one valve of the central valve unit, wherein the fluid is a gas, a pressurized gas, or a liquid.

21. The method for propelling a probe within a lumen as in claim 19, further comprising the procedure of inflating at least a portion of said sleeve with said fluid, through said at least one valve when advancing or retracting said sheath within said lumen.

22. The method for propelling a probe within a lumen as in claim 19, further comprising the procedure of inflating a distal side of said sleeve using said central valve unit to insert the probe, and a proximal side of said sleeve to extract the probe.

23. The method for propelling a probe within a lumen as in claim 19, further comprising the procedures of: extending/expanding said sleeve beyond a distal edge of said sheath when advancing said sheath forward; and extending/expanding said sleeve beyond a proximal edge of said sheath when receding said sheath backwards.

24. The method for propelling a probe within a lumen as in claim 19, further comprising selectively inflating or deflating said sleeve for sheath advancement/receding or for instrument insertion/retracting/operation.

25. The method for propelling a probe within a lumen as in claim 19, wherein said at least one valve comprises a distal valve and a proximal valve, further comprising the procedures of: extending/expanding said sleeve beyond a distal edge of said sheath, as introducing fluid into a distal portion of said sheath through said distal valve and said sheath advances forward; and extending/expanding said sleeve beyond a proximal edge of said sheath, as introducing fluid into a proximal portion of said sheath through said proximal valve and said sheath advances backward.

26. The method for propelling a probe within a lumen as in claim 19, further comprising the procedure of blocking by a separating mechanism the passage of fluid directly between said distal valve and said proximal valve.

27. The method for propelling a probe within a lumen as in claim 19, further comprising the procedure of pushing and/or pulling said sleeve inside said sheath for pushing and/or pulling said sheath inside said lumen.

28. The method for propelling a probe within a lumen as in claim 19, further comprising the procedure of sliding the probe by a propulsion mechanism, wherein said mechanism comprises at least one selected from the list consisting of:
  sprocket wheel;
  toothed mechanism
  friction based mechanism;
  indented sleeve
  grooved sheath
  slotted sheath;
  externally serrated/indented sheath; and
  internally serrated/indented sheath.

29. The method for propelling a probe within a lumen as in claim 19, further comprising the procedure of selectively inserting a rod within the central bore of said sheath, wherein said rod comprises at least one of:
  bulbous head for facilitating push/pull of said sheath;
  expandable head for facilitating push/pull of said sheath;
  expandable head for selectively blocking fluid flow inside said sleeve at a blocking location disposed within the bore of said sheath; and
  instrument for examination, diagnosis and treatment of the patient.

30. The method according to claim 19, further comprising providing an instrument for examination, diagnosis and treatment of the patient, the instrument:
  disposed within the central bore of the tubular sheath outside of the flexible sleeve;
  disposed within the central bore of the tubular sheath within the flexible sleeve, the instrument inserted between the tubular sheath and the flexible sleeve;
  embedded in the tubular sheath;
  deployed beside the tubular sheath within the flexible sleeve; or
  deployed beside the tubular sheath outside the flexible sleeve.

31. The method for propelling a probe within a lumen as in claim 19, wherein said sheath comprises a perforated sheath allowing passage of fluid there through.

32. The method for propelling a probe within a lumen as in claim 19, further comprising the procedure of retracting said sleeve from said sheath by a pulling wire.

33. The method according to claim 19, further comprising angulating a tip of the tubular sheath within the internal lumen using pulling wires or steering the tubular sheath within the internal lumen using pulling wires.

34. The method according to claim 19, wherein a portion of said sleeve comprises a variable diameter to accommodate a variable diameter of the internal lumen.

35. The method for propelling a probe within a lumen as in claim 19, further comprising coating/depositing a face of said sleeve with an anesthetic or other medical substance.

36. The method according to claim 19, further comprising positioning the central valve unit adjacent an anus of a patient during operation of the hollow probe by connecting an anus adaptor to a distal end of the central valve unit.

* * * * *